(12) United States Patent
Agarwal et al.

(10) Patent No.: US 12,383,530 B2
(45) Date of Patent: *Aug. 12, 2025

(54) PHARMACEUTICAL COMBINATION FOR THE TREATMENT OF MELANOMA

(71) Applicant: Piramal Enterprises Limited, Mumbai (IN)

(72) Inventors: Veena Agarwal, Mumbai (IN); Giridharan Periyasamy, Bangalore (IN); Maggie Rathos, Mumbai (IN); Ankita Srivastava, Mumbai (IN); Sreesha Srinivasa, Mumbai (IN)

(73) Assignee: PIRAMAL ENTERPRISES LIMITED, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 18/497,653

(22) Filed: Oct. 30, 2023

(65) Prior Publication Data

US 2024/0165076 A1 May 23, 2024

Related U.S. Application Data

(63) Continuation of application No. 17/168,876, filed on Feb. 5, 2021, now Pat. No. 11,839,591, which is a continuation of application No. 14/904,407, filed as application No. PCT/IB2014/063022 on Jul. 11, 2014, now Pat. No. 11,007,174.

(60) Provisional application No. 61/845,749, filed on Jul. 12, 2013.

(51) Int. Cl.
| | | |
|---|---|---|
| A61K 31/4025 | (2006.01) | |
| A61K 31/437 | (2006.01) | |
| A61K 31/506 | (2006.01) | |
| A61K 31/519 | (2006.01) | |
| A61K 45/06 | (2006.01) | |

(52) U.S. Cl.
CPC ........ *A61K 31/4025* (2013.01); *A61K 31/437* (2013.01); *A61K 31/506* (2013.01); *A61K 31/519* (2013.01); *A61K 45/06* (2013.01)

(58) Field of Classification Search
CPC .............. A61K 31/4025; A61K 31/437; A61K 31/506; A61K 31/519; A61K 45/06
See application file for complete search history.

(56) References Cited

U.S. PATENT DOCUMENTS

| | | |
|---|---|---|
| 4,900,727 A | 2/1990 | Kattige |
| 5,116,954 A | 5/1992 | Briet |
| 5,284,856 A | 2/1994 | Naik |
| 5,723,313 A | 3/1998 | Sherr |
| 5,733,920 A | 3/1998 | Mansuri |
| 5,849,733 A | 12/1998 | Kim |
| 6,699,854 B2 | 3/2004 | Wang |
| 7,056,942 B2 | 6/2006 | Hildesheim |
| 7,271,193 B2 | 9/2007 | Lal |
| 7,772,207 B2 | 8/2010 | Green |
| 7,884,127 B2 | 2/2011 | Lal |
| 7,915,301 B2 | 3/2011 | Lal |
| 8,304,449 B2 | 11/2012 | Lal |
| 8,563,596 B2 | 10/2013 | Sivakumar |
| 8,822,526 B2 | 9/2014 | Rathos |
| 8,895,605 B2 | 11/2014 | Rathos |
| 2004/0106581 A1 | 6/2004 | Lal |
| 2005/0176696 A1 | 8/2005 | Dorr |
| 2005/0267066 A1 | 12/2005 | Gianella-Borradori |
| 2006/0247305 A1 | 11/2006 | Wang |
| 2007/0015802 A1 | 1/2007 | Lal |
| 2008/0108690 A1 | 5/2008 | Lal |
| 2010/0143350 A1 | 6/2010 | Green |
| 2010/0152129 A1 | 6/2010 | Giridharan |
| 2010/0179210 A1 | 7/2010 | Sivakumar |
| 2010/0305057 A1 | 12/2010 | Rathos |
| 2011/0136873 A1 | 6/2011 | Lal |
| 2012/0046334 A1 | 2/2012 | Rathos |
| 2012/0321637 A1 | 12/2012 | Dong |
| 2013/0045993 A1 | 2/2013 | Lal |
| 2014/0112918 A1 | 4/2014 | Agarwal |

FOREIGN PATENT DOCUMENTS

| | | |
|---|---|---|
| CN | 101472888 A | 7/2009 |
| JP | 2009541294 A | 11/2009 |
| JP | 2013543008 A | 11/2013 |

(Continued)

OTHER PUBLICATIONS

IN2008MU00699 (Year: 2009).*
Office action mailed Dec. 29, 2020 in connection with Argentina Patent Application No. 20140102577.
Office action mailed Sep. 17, 2019 in connection with Argentina Patent Application No. 20140102577.
Office action mailed Nov. 16, 2018 in connection with Australian Patent Application No. 2014288857.
Office action mailed Dec. 18, 2018 in connection with Japanese Patent Application No. 2016-524936.
Office action mailed Sep. 24, 2019 in connection with Japanese Patent Application No. 2019-141995.

(Continued)

*Primary Examiner* — Jeffrey S Lundgren
*Assistant Examiner* — Ibrahim D Bori
(74) *Attorney, Agent, or Firm* — Morgan, Lewis & Bockius LLP

(57) ABSTRACT

The present invention relates to a pharmaceutical combination comprising a cyclin dependent kinase (CDK) inhibitor represented by a compound of formula I (as described herein) or a pharmaceutically acceptable salt thereof; and at least one anticancer agent selected from a BRAF inhibitor or a MEK inhibitor, for use in the treatment of melanoma. The present invention also relates to a method for the treatment of melanoma comprising administering to a subject in need thereof, a therapeutically effective amount of a CDK inhibitor and a therapeutically effective amount of at least one anticancer agent selected from a BRAF inhibitor or a MEK inhibitor.

19 Claims, 12 Drawing Sheets

(56) References Cited

FOREIGN PATENT DOCUMENTS

| | | | |
|---|---|---|---|
| WO | 2000/61187 | A1 | 10/2000 |
| WO | 2001/83469 | A1 | 11/2001 |
| WO | 2004/004632 | A2 | 1/2004 |
| WO | 2007002325 | A1 | 1/2007 |
| WO | 2007/148158 | A1 | 12/2007 |
| WO | 2008/007169 | A1 | 11/2008 |
| WO | 2008/139271 | A2 | 11/2008 |
| WO | 2010/128443 | A1 | 11/2010 |
| WO | 2011/104584 | A1 | 9/2011 |
| WO | 2012027438 | A1 | 3/2012 |
| WO | 2012/066508 | A1 | 5/2012 |
| WO | 2012068468 | A1 | 5/2012 |
| WO | 2012/123889 | A1 | 9/2012 |
| WO | 2012/164497 | A1 | 12/2012 |
| WO | 2012/176163 | A1 | 12/2012 |
| WO | 2013/105056 | A1 | 7/2013 |
| WO | 2014/049515 | A1 | 4/2014 |
| WO | 2014/128523 | A1 | 8/2014 |
| WO | 2015/004636 | A1 | 1/2015 |
| WO | 2015/181737 | A1 | 12/2015 |

OTHER PUBLICATIONS

EP Application No. 14822283 Decision to Grant; dated Nov. 4, 2019.
EP Application No. 14822283 Intention to Grant; dated Nov. 20, 2018.
EP Application No. 14822283 Search Opinion; dated May 9, 2016.
EP Application No. 14822283 Supplemental European Search Report; dated Mar. 9, 2017.
Chellappan et al., AACR 103rd Annual Meeting, Abstract 5598, 2012.
Dong et al., Melanoma—From Early Detection to Treatment, Chapter 1, published Jan. 30, 2013, pp. 1-27.
Office Action mailed Aug. 24, 2021 in JP Application No. 2020-152028, 14 pages.
Office Action mailed Sep. 1, 2021 in TW Application No. 108142557, 11 pages.
Office Action mailed May 12, 2022 in Argentina Application No. 20140102577, 9 pages.
Office Action mailed Jul. 15, 2022 in Chinese Application No. 201911007262.X, 12 pages.
Denial Report mailed Jan. 6, 2023 in Argentina Application No. 20140102577, 8 pages.
Second Office Action mailed Feb. 1, 2023 in Chinese Application No. 201911007262.X, 4 pages.
Notice of Reasons for Rejection issued in Japanese Patent Application No. 2022-026851 dated Mar. 14, 2023, 5 pages.
Examination Notice issued Apr. 19, 2023 in TW Application No. 111106633, 10 pages.
Third Office Action issued Jun. 22, 2023 in CN Application No. 201911007262X, 4 pages.
Decision of Rejection issued Aug. 15, 2023 in Japanese Application No. 2022-026851, 4 pages.
Notification of Grant issued Sep. 11, 2023 in Chinese Application No. 201911007262.X, 1 page.
Giridharan, "Novel Synergistic Combination of Gemcitabine with P276-00 or P1446A in Treatment of Cancer," IN2008MU00699, Jun. 12, 2009.
PubChem CID 117071100 (Year: 2006).
Office Action mailed Oct. 25, 2022 in U.S. Appl. No. 17/168,876, 12 pages.
Jung, et al. The cyclin-dependent kinase inhibitor flavopiridol potentiates gamma-irradiation-induced apoptosis in colon and gastric cancer cells. Clin Cancer Res. Dec. 1, 2003; 9(16 Pt 1):6052-61.
Kelland. Expert Opinion on Investigational Drugs. Ashley Publications Ltd. 2000; 9(12):2903-2911.
Kim, et al. Enhancement of radiation effects by combined docetaxel and flavopiridol treatment in lung cancer cells. Radiother Oncol. May 2004; 71(2):213-21.
Kim, et al. Enhancement of radiation effects by flavopiridol in uterine cervix cancer cells. Cancer Res Treat. Jun. 2005; 37(3):191-5.
Kleinberg, et al. Chemoradiotherapy for localized esophageal cancer: regimen selection and molecular mechanisms of radiosensitization. Nat Clin Pract Oncol. May 2007; 4(5):282-94.
Kohza To, et al. Overexpression of cyclin E and cyclin-dependent kinase 2 is correlated with development of hepatocellular carcinomas. Hepatol Res. Sep. 2001; 21(1):27-39.
Koontongkaew, et al. Alterations of p53, pRb, cyclin D(I) and cdk4 in human oral and pharyngeal squamous cell carcinomas. Oral Oncol. Jul. 2000; 36(4):334-9.
Larget, et al. A convenient extension of the Wessely-Moser rearrangement for the synthesis of substituted alkylaminoflavones as neuroprotective agents in vitro. Bioorg Med Chem Lett. Apr. 17, 2000; 10(8):835-8.
Li, et al. Expression of cyclin E and cyclin-dependent kinase 2 correlates with metastasis and prognosis in colorectal carcinoma. Hum Pathol. Sep. 2001; 32(9):945-53.
Li, et al. Selective sensitization of retinoblastoma protein-deficient sarcoma cells to doxorubicin by flavopiridol-mediated inhibition of cyclin-dependent kinase 2 kinase activity. Cancer Res. Mar. 15, 2001; 61(6):2579-82.
Losiewicz, et al. Potent inhibition of CDC2 kinase activity by the flavonoid L86-8275. Biochem Biophys Res Commun. Jun. 15, 1994; 201(2):589-95.
Marchini, et al. Absence of deletions but frequent loss of expression of p16INK4 in human ovarian tumours. Br J Cancer. 1997; 76(2):146-9.
Matsumoto, et al. Comparison of deregulated expression of cyclin D1 and cyclin E with that of cyclin-dependent kinase 4 (CDK4) and CDK2 in human oesophageal squamous cell carcinoma. Br J Cancer. Apr. 1999; 80(1-2):256-61.
Meijer, et al. Properties and potential applications of chemical inhibitors of cyclin-dependent kinases. Pharmacol. Ther. 1999; 82(2-3):279-284.
Moore, et al. Erlotinib plus gemcitabine compared with gemcitabine alone in patients with advanced pancreatic cancer: a phase III trial of the National Cancer Institute of Canada Clinical Trials Group. J Clin Oncol. May 20, 2007; 25 (15):1960-6. Epub Apr. 23, 2007.
Naik, et al. An antiinflammatory cum immunomodulatory piperidinylbenzopyranone from dysoxylum binectariferum: isolation, structure and total synthesis. Tetrahedron. 1998; 44(7):2081-2086.
Nelson, et al. Lapatinib: a novel dual tyrosine kinase inhibitor with activity in solid tumors. Ann Pharmacother. Feb. 2006; 40(2):261-9. Epub Jan. 17, 2006.
Notice of allowance dated Apr. 18, 2007 for U.S. Appl. No. 10/611,539.
Notice of allowance dated May 23, 2012 for U.S. Appl. No. 13/026,503.
Notice of allowance dated Jun. 1, 2012 for U.S. Appl. No. 13/026,503.
Notice of allowance dated Jun. 5, 2013 for U.S. Appl. No. 12/305,815.
Notice of allowance dated Aug. 1, 2014 for U.S. Appl. No. 13/318,235.
Notice of allowance dated Oct. 15, 2010 for U.S. Appl. No. 11/530,272.
Notice of allowance dated Nov. 12, 2010 for U.S. Appl. No. 11/779,577.
Notice of allowance dated Nov. 20, 2013 for U.S. Appl. No. 12/600,019.
Office action dated Jan. 30, 2007 for U.S. Appl. No. 10/611,539.
Office action dated Feb. 10, 2010 for U.S. Appl. No. 12/305,815.
Office action dated Feb. 26, 2010 for U.S. Appl. No. 11/530,272.
Office action dated Apr. 4, 2011 for U.S. Appl. No. 13/026,503.
Office action dated Apr. 14, 2014 for U.S. Appl. No. 13/318,235.
Office action dated Apr. 16, 2009 for U.S. Appl. No. 11/779,577.
Office action dated Apr. 19, 2006 for U.S. Appl. No. 10/611,539.
Office action dated Jun. 12, 2012 for U.S. Appl. No. 12/600,019.
Office action dated Jun. 12, 2013 for U.S. Appl. No. 13/585,006.
Office action dated Jul. 24, 2008 for U.S. Appl. No. 11/779,577.
Office action dated Aug. 3, 2011 for U.S. Appl. No. 12/305,815.
Office action dated Aug. 27, 2010 for U.S. Appl. No. 11/779,577.
Office action dated Sep. 4, 2009 for U.S. Appl. No. 11/530,272.

(56) References Cited

OTHER PUBLICATIONS

Office action dated Oct. 7, 2011 for U.S. Appl. No. 12/600,019.
Office action dated Oct. 11, 2012 for U.S. Appl. No. 12/305,815.
Office action dated Nov. 4, 2005 for U.S. Appl. No. 10/611,539.
Office action dated Nov. 22, 2011 for U.S. Appl. No. 13/026,503.
Office action dated Dec. 5, 2012 for U.S. Appl. No. 13/585,006.
Office action dated Dec. 14, 2009 for U.S. Appl. No. 11/779,577.
Ongkeko, et al. Inactivation of Cdc2 increases the level ofapoptosis induced by DNA damage. J Cell Sci. Aug. 1995; 108 (Pt 8):2897-904.
Ortega, et al. Cyclin D-dependent kinases, INK.4 inhibitors and cancer. Biochim Biophys Acta. Mar. 14, 2002; 1602 (1):73-87.
Parker, et al. Early induction of apoptosis in hematopoietic cell lines after exposure to flavopiridol. Blood. Jan. 15, 1998; 91(2):458-65.
Patel, et al. Flavopiridol, a novel cyclin-dependent kinase inhibitor, suppresses the growth of head and neck squamous cell carcinomas by inducing apoptosis. J Clin Invest. Nov. 1, 1998; 102(9):1674-81.
Perez-Roger, et al. Inhibition of cellular proliferation by drug targeting of cyclin-dependent kinases. Curr Pharm Biotechnol. Jul. 2000; 1(1):107-16.
PLATINOL-AQ (cisplatin injection) package insert. Revised Apr. 2006.
American Academy of Dermatology, 2016, https://www.aad.org/public/spot-skin-cancer/learn-about-skin-cancer/types-of-skin-cancer.
Co-pending U.S. Appl. No. 15/206,185, filed Jul. 8, 2016.
Harrington et al., Phase I Study of Lapatinib in Combination with Chemoradiation in Patients With Locally Advanced Squamous Cell Carcinoma of the Head and Neck, 2009, Journal of Clinical Oncology, vol. 27, No. 7, pp. 11 00-11 07.
National Cancer Institute, 2016, http://www.cancer.gov/publications/dictionaries/cancer-terms?cdrid=46595.
Office Action dated Feb. 9, 2016 for U.S. Appl. No. 14/122,922.
Williamson et al., Phase II Evaluation of Sorafenib in Advanced and Metastatic Squamous Cell Carcinoma of the Head and Neck: Southwest Oncology Group Study S0420, 2010, Journal of Clinical Oncology, vol. 28, No. 20, pp. 3330-3336.
European Search Report dated Mar. 20, 2017 for EP Application No. 14822283.9.
Kalpana, J. et al, "P1446A-05: a new oral cyclin-dependent kinase inhibitor with potent preclinical antitumor activity", Cancer Research, vol. 72, No. Suppl. 8, Apr. 2012, XP2671277, &103rd Annual meeting of the American-association-for-cancer-research; Chicago, IL, USA; Mar. 31-Apr. 4, 2012, tables 1,2.
European Search Report dated Apr. 21, 2010 for EP Application No. 07735911.5.
European Search Report dated May 6, 2015 for EP Application No. 12738184.6.
Briet et al., U.S. Pat. No. H1427 H, Publication date Apr. 4, 1995.
Ascierto, et al. The role of BRAF V6OO mutation in melanoma. J Transl Med. Jul. 9, 2012;10:85.
Badone, et al. Palladium-catalyzed coupling of aryl arenesulfonates with organostannanes. J. Org. Chem. 1992; 57 (23):6321-6323.
Baker. Molecular rearrangement of some o-acyloxyacetophenones and the mechanism of the production of 3-acylchromones. Journal of the Chemical Society (Resumed) (1933): 1381-1389.
Barnes, et al. Development of a catalytic enantioselective conjugate addition of 1,3-dicarbonyl compounds to nitroalkenes for the synthesis of endothelin-A antagonist ABT-546. Scope, mechanism, and further application to the synthesis of the antidepressant rolipram. J Am Chem Soc. Nov. 6, 2002;124(44):13097-105.
Bride et al, "Advances in Chemotherapy for Head and Neck Cancer," Oral Oncology, Apr. 18, 2010, pages vol. 46, No. 6, Elsevier Science, Oxford, GB.
Bonner, et al. Radiotherapy plus cetuximab for squamous-cell carcinoma of the head and neck. N Engl J Med. Feb. 9, 2006;354(6):567-78.
Bristol-Myers Squibb Patient Information for Taxol, Mar. 2003.
Buolamwini. Cell cycle molecular targets in novel anticancer drug discovery. Curr Pharm Des. Mar. 2000;6 (4):379-92.

Burtness, et al. Phase III randomized trial of cisplatin plus placebo compared with cisplatin plus cetuximab in metastatic/recurrent head and neck cancer: an Eastern Cooperative Oncology Group study. J Clin Oncol. Dec. 1, 2005;23(34):8646-54.
Chapman, et al. Improved survival with vemurafenib in melanoma with Braf V600E mutation. N Engl J Med. Jun. 30, 2011; 364(26):2507-16.
Chen, et al. A new facile method for the synthesis of 1-arylimidazole-5-carboxylates. Tetrahedron Letters. 2000; 41 (29):5453-5456.
Chou. Theoretical basis, experimental design, and computerized simulation of synergism and antagonism in drug combination studies. Pharmacol Rev. Sep. 2006; 58(3):621-81.
Davies, et al. Structure-based design of cyclin-dependent kinase inhibitors. Pharmacol Ther. Feb.-Mar. 2002;. 93 (2-3):125-33.
Dhomen, et al. BRAF signaling and targeted therapies in melanoma. Hematol Oncol Clin North Am. Jun. 2009;23 (3):529-45.
Dong, et al. Cyclin D1-CDK4 complex, a possible critical factor for cell proliferation and prognosis in laryngeal squamous cell carcinomas. Int J Cancer. Jul. 20, 2001; 95(4):209-15.
Dong, et al. The overexpression of cyclin-dependent kinase (CDK) 2 in laryngeal squamous cell carcinomas. Anticancer Res. Jan.-Feb. 2001; 21(1A):103-8.
Dorland's Pocket Medical Dictionary. W.B. Saunders Co. 1989; p350.
El Rayes, et al. A phase I study of flavopiridol and docetaxel. Invest New Drugs. Jul. 2006; 24(4):305-10.
Elsayed, et al. Selected novel anticancer treatments targeting cell signaling proteins. Oncologist. 2001; 6(6):517-37.
Elser et al., "A Phase II Study of Sorafenib (BAY 43-9006) in Recurrent and/or Metastatic Squamous Cell Carcinoma of the Head and Neck (SCCHN) and Nasopharyngeal Cancer (NPC): Final Results," European Journal of Cancer, Supplement, Pergamon, Nov. 8, 2006, p. 18, vol. 4, No. 12, Oxford, GB.
Falb, et al. A Convenient Synthesis of Chiral Oxazolidin-2-Ones and Thiazolidin-2-Ones and an Improved Preparation of Triphosgene. Synthetic Communications, 1993; 23(20):2839-2844.
Fischer, et al. CDK inhibitors in clinical development for the treatment of cancer. Expert Opin Investig Drugs. Jun. 2003; 12(6):955-70.
Flaherty, et al. Inhibition of mutated, activated BRAF in metastatic melanoma. N Engl J Med. Aug. 26, 2010; 363 (9):809-19.
Fong, et al. Early deregulation of the the p16ink4a-cyclin DI/cyclin-depen9,ent kinase 4-retinoblastoma pathway in cell proliferation-driven esophageal tumorigenesis in zinc-deficient rats. Cancer Res. Aug. 15, 2000; 60(16):4589-95.
Goffin, et al. P-348 A phase I trial of gemcitabine followed by flavopiridol in patients with solid tumors. Lung Cancer 41 (2003): S179-S180.
Gross, et al. A stereocontrolled approach to substituted piperidones and piperidines: flavopiridol D-ring analogs. Tetrahedron Letters. 2001; 42(9): 1631-1633.
He, et al. Lack of p16INK4 or retinoblastoma protein (pRb), or amplification- associated overexpression of cdk4 is observed in distinct subsets of malignant glial tumors and cell lines. Cancer Res. Nov. 1, 1995; 55(21):4833-6.
Higa, et al. Lapatinib in the treatment of breast cancer. Expert Rev Anticancer Ther. Sep. 2007; 7(9):1183-92.
Hirama, et al. Role of the cyclin-dependent kinase inhibitors in the development of cancer. Blood. Aug. 1, 1995; 86 (3):841-54.
Hiroyuki, et al. Detection of cyclin D 1/Cdk 4 mRNA and proteins of the head and neck cancer. (Abstract). Oto-Rhino-Laryngology Tokyo. 1999; 42:276-282.
Rodi, et al. Improved survival with ipilimumab in patients with metastatic melanoma. N Engl J Med. Aug. 19, 2010; 363 (8):711-23.
Hosoi, et al. Evidence for cdk5 as a major activity phosphorylating tau protein in porcine brain extract. J Biochem. Apr. 1995; 117(4):741-9.
International search report and written opinion dated Jun. 24, 2004 for PCT/IN2003/000234.
International search report and written opinion dated Mar. 15, 2007 for PCT/IB2006/052002.
International search report and written opinion dated Aug. 12, 2010 for PCT/IB2010/051921.

(56) References Cited

OTHER PUBLICATIONS

International search report and written opinion dated Oct. 27, 2014 for PCT/IB2014/063022.
International search report and written opinion dated Nov. 21, 2008 for PCT/IB2007/051841.
International Search Report for PCT/IB2012/052698, dated Sep. 10, 2012.
Jemal, et al. Cancer statistics, 2008. CA Cancer J Clin. Mar.-Apr. 2008; 58(2):71-96.
Rofstad, et al. Hypoxia-induced treatment failure in advanced squamous cell carcinoma of the uterine cervix is primarily due to hypoxia-induced radiation resistance rather than hypoxia-induced metastasis. Br J Cancer. Aug. 2000; 83(3):354-9.
Roskoski, et al. MEK1/2 dual-specificity protein kinases: structure and regulation. Biochem Biophys Res Commun. Jan. 6, 2012; 417(1):5-10.
Sausville, et al. Cyclin-dependent kinases: initial approaches to exploit a novel therapeutic target. Pharmacol. Ther. 1999; 82(2-3):285-292.
Sausville. Cyclin-dependent kinases: novel targets for cancer treatment. Developmental Therapeutics Program. 1999; 9-21.
Schwartz, et al. Phase I study of the cyclin-dependent kinase inhibitor flavopiridol in combination with paclitaxel in patients with advanced solid tumors. J Clin Oncol. Apr. 15, 2002; 20(8):2157-70.
Schwartz, et al. Phase I trial of sequential paclitaxel and the cyclin dependent kinase inhibitor flavopiridol. Proc Am Soc Clin Oncol. vol. 18. 1999. p. 160A.
Senderowicz. Small molecule modulators of cyclin-dependent kinases for cancer therapy. Oncogene. Dec. 27, 2000; 19(56):6600-6.
Shapiro, et al. A phase II trial of the cyclin-dependent kinase inhibitor flavopiridol in patients with previously untreated stage IV non-small cell lung cancer. Clin Cancer Res. Jun. 2001; 7(6):1590-9.
Smalley, et al. Increased cyclin DI expression can mediate BRAF inhibitor resistance in BRAF V6OOE-mutated melanomas. Mol Cancer Ther. Sep. 2008; 7(9):2876-83.
Smalley, et al. Integrating BRAF/MEK inhibitors into combination therapy for melanoma. Br J Cancer. Feb. 10, 2009; 100(3):431-5.
Soni, et al. Selective in vivo and in vitro effects of a small molecule inhibitor of cyclin-dependent kinase 4. J Natl Cancer Inst. Mar. 21, 2001; 93(6):436-46.
Soulieres et al, "Multicenter Phase II Study of Erlotinib, an Oral Epidermal Growth Factor Receptor Tyrosine Kinase Inhibitor, in Patients With Recurrent or Metastatic Squamous Cell Cancer of the Head and Neck," of Clinical Oncology, Jan. 1, 2004, pp. 77-85, vol. 22, No. 1, American Society of Clinical Oncology, United States.
Stadler, et al. Flavopiridol, a novel cyclin-dependent kinase inhibitor, in metastatic renal cancer: a University of Chicago Phase II Consortium study. J Clin Oncol. Jan. 2000; 18(2):371-5.
Study of an oral Cdk inhibitor with an oral BRAF inhibitor in patients with advanced or inoperable malignant melanoma with BRAF mutation. NCT01841463. Clinicaltrials.gov. Updated Apr. 25, 2013. 7 pages. http://clinicaltrials.gov/archive/NCT01841463/2013_04_25.
Tan, et al. Phase I clinical and pharmacokinetic study of flavopiridol administered as a daily I-hour infusion in patients with advanced neoplasms. J Clin Oncol. Oct. 1, 2002; 20(19):4074-82.
Taxol injection package insert. Revised Jul. 2007.
Toogood. Cyclin-dependent kinase inhibitors for treating cancer. Med Res Rev. Nov. 2001; 21(6):487-98.
Tsuritani, et al. Radical [3+2] annulation of N-allyl-N-chlorotosylamide with alkenes via atom-transfer process. Org Lett. Aug. 23, 2001; 3(17):2709-11.
Tyagi, et al. The cancer preventive flavonoid silibinin causes hypophosphorylation of Rb/p 107 and Rb2/p130 via modulation of cell cycle regulators in human prostate carcinoma DU145 cells. Cell Cycle. Mar.-Apr. 2002; 1(2):137-42.
Venkataraman, et al. A Synthesis of Flavones at Room Temperature. J. Indian Chem. Soc.; Dec. 1933; pp. 214-215.
Venkataraman, et al. Synthetical Experiments in the Flavone and Isoflavone groups. Symposium Sep. 26-27, 1938. vol. V—No. 2; Published Jun. 5, 1939; pp. 253-260.
Vippagunta, et al. Crystalline solids. Adv Drug Deliv Rev. May 16, 2001; 48(1):3-26.
Wang, et al. Synthesis and biologic properties of hydrophilic sapphyrins, a new class of tumor-selective inhibitors of gene expression, Mol. Cancer, 2007, Jan. 19; 6:9.
Wei, et al. CDK4 gene amplification in osteosarcoma: reciprocal relationship with INK4A gene alterations and mapping of 12q13 amplicons. Int J Cancer. Jan. 18, 1999; 80(2): 199-204.
Wheeler. Flavone. Organic Syntheses Collective Volumes. 1963; 4:478. http://www.orgsyn.org/demo.aspx?prep=CV4P0478.
Wilhelm, et al. Preclinical overview of sorafenib, a multikinase inhibitor that targets both Raf and VEGF and PDGF receptor tyrosine kinase signaling. Mol Cancer Ther. Oct. 2008; 7(10):3129-40.
Wood, et al. A unique structure for epidermal growth factor receptor bound to GW572016 (Lapatinib): relationships among protein conformation, inhibitor off-rate, and receptor activity in tumor cells. Cancer Res. Sep. 15, 2004; 64 (18):6652-9.
Yao, et al. Infrequent mutation of the p 16/MTS1 gene and overexpression of cyclin-dependent kinase 4 in human primary soft-tissue sarcoma. Clin Cancer Res. Apr. 1998; 4(4): 1065-70.
Zhang, et al. Concurrent overexpression of cyclin DI and cyclin-dependent kinase 4 (Cdk4) in intestinal adenomas from multiple intestinal neoplasia (Min) mice and human familial adenomatous polyposis patients. Cancer Res. Jan. 1, 1997; 57(1):169-75.
Office action mailed Dec. 24, 2020 in connection with Taiwan Patent Application No. 108142557.
Decision of Rejection mailed May 11, 2020 in connection with Japanese Patent Application No. 2019-141995.
Cancer Research, Apr. 2012, vol. 72, Issue 8, Supplement, Abstract: 5598, DOI: 10.1158/1538-7445.AM2012-3054.
Journal of Investigative Dermatology, 2011, vol. 131, Supplement 1, p. S121, 726 Abstract, 00110.1038i jid.201175.
Taiwan Office Action for Application No. 103123951; received Nov. 16, 2018.
English translation of Taiwan Office Action for Application No. 103123951; received Nov. 16, 2018.
Chinese Office Action for Application No. 2014800505076; dated Sep. 25, 2018.
English translation of Chinese Office Action for Application No. 2014800505076; dated Oct. 26, 2018.
STN Registry 920113-03-07, Feb. 9, 2007.
Clin Cancer Res; 19(16) Aug. 15, 2013; Salama et al. BRAF in Melanoma: Current Strategies and Future Directions.
Israeli Patent Application No. 243572, Notice of Deficiencies dated Jun. 21, 2018, 6 pages.
Ali Akbar et al. "Identification of Flavopiridol Analogues that Selectively Inhibit Positive Transcription Elongation Factor (P-TEFb) and Block HIV-1 Replication" Chembiochem 10(12):2072-2080, Aug. 17, 2009.
Chinese Patent Application No. 201480050507.6 First Office Action dated Apr. 5, 2017, 12 pages.
Chinese Patent Application No. 201480050507.6 Second Office Action dated Feb. 24, 2018, 3 pages.
International Patent Application No. PCT/IB2014/063022 International Preliminary Report on Patentability dated Jan. 21, 2016, 7 pages.
Japanese Patent Application No. 2016-524936 Notice of Reasons for Rejection dated Feb. 27, 2018, 7 pages.
Taiwanese Patent Application No. 103123951 Examination Notification dated Mar. 5, 2018, 9 pages.
Vidwans et al., "A Melanoma Molecular Disease Model," PLoS ONE, 2011, 6(3), e18257, 1-10.
Kwong et al., "Oncogenic NRAS signaling differentially regulates survival and proliferation in melanoma," Nature Medicine, 2012, 18(10), 1503-1510.

* cited by examiner

PHARMACEUTICAL COMBINATION FOR THE TREATMENT OF MELANOMA

CROSS-REFERENCE TO RELATED APPLICATIONS

This application is a continuation of U.S. patent application Ser. No. 17/168,876, filed on Feb. 5, 2021, granted as U.S. Pat. No. 11,839,591, which is a continuation of U.S. patent application Ser. No. 14/904,407, filed on Jan. 11, 2016, granted as U.S. Pat. No. 11,007,174, which is a U.S. National Stage entry filing of International Patent Application No. PCT/IB2014/063022, filed on Jul. 11, 2014, which claims the benefit of U.S. Provisional Patent Application No. 61/845,749, filed on Jul. 12, 2013, all of which are incorporated by reference herein in their entireties.

FIELD OF THE INVENTION

The present invention relates to a pharmaceutical combination comprising a CDK (cyclin dependent kinase) inhibitor represented by a compound of formula I (as described herein) or a pharmaceutically acceptable salt thereof and at least one anticancer agent selected from a BRAF (serine-threonine protein kinase B-raf) inhibitor or a MEK (mitogen activated protein kinase) inhibitor, for use in the treatment of melanoma. The invention also relates to a method of treating melanoma using the pharmaceutical combination.

BACKGROUND OF THE INVENTION

Melanoma is the most serious type of skin cancer. Melanoma, in fact, is a malignant tumor that originates in cells called melanocytes, which are pigment producing cells. It occurs most often in the skin but may also develop in the eye or in the lining of the nose, mouth or genitals. Subsequently, melanoma can spread to internal organs. When melanoma occurs in the skin it is referred to as cutaneous melanoma. Melanoma when occurs in the eye, is called ocular or intraocular melanoma. Incidence of melanoma is increasing worldwide, it is reported that malignant melanoma is responsible for 80% of skin cancer deaths (N. Engl. J. Med., 2010, 363, 8, 711-723).

When melanoma spreads, cancer cells are often found in the lymph nodes. When the cancer reaches the lymph nodes, it is an indication that the cancer cells may have spread to other parts of the body such as the liver, lungs or brain, giving rise to metastatic melanoma. In fact, melanoma metastases are highly aggressive and the survival time for patients with metastatic melanoma averages 3-15 only. Unfortunately, effective treatment exists months no for metastatic melanoma. Early diagnosis and prompt surgical removal are the possible options for patients for a possible cure. The therapeutic regimen for metastatic melanoma initially comprised of the drugs such as interleukin-2, dacarbazine, temozolomide, fotemustine and carboplatin but each is associated with a poor response rate and poor overall survival. For instance, dacarbazine was found to be associated with a response rate of 7-12% and a median overall survival of 5-8 months after initiation of the treatment (N. Engl. J. Med., 2011, 364, 26, 2507-2516).

In a study of the mitogen-activated protein (MAP) kinase pathway in a large panel of common cancers, it has been found that 40-60% of melanomas carry an activating mutation in the gene encoding the serine-threonine protein kinase B-raf (BRAF). Among the BRAF mutations observed in melanoma, over 90% are at codon 600, and among these, over 90% are a single nucleotide mutation resulting in substitution of glutamic acid for valine (BRAFV600E). The second most common mutation is BRAFV600K substituting lysine for valine, which represents 5-6% of melanomas, followed by BRAFV600R (substituting arginine for valine) and BRAFV600D (substituting aspartic acid for valine) (Journal of Translational Medicine, 2012, 10, 85, 1-9).

BRAF inhibitors have been found to be effective in tumor shrinkage in the majority of patients with BRAF mutant melanoma at low nanomolar concentrations. The limiting factors in efficacy are the drug resistance and the progression-free survival which is restricted to 5-7 months. A few examples of potent BRAFV600 inhibitors include BAY43-9006 (sorafenib, Bayer), vemurafenib (PLX4032, Plexxikon; RG7204, RO5185426, Hofmann-LaRoche), GDC-0879 (GlaxoSmithKline), dabrafenib (GSK2118436, GlaxoSmithKline), PLX4720 (Hofmann-LaRoche), BMS-908662 (XL281, Bristol-Myers Squibb), LGX818 (Novartis), PLX3603 (RO5212054, Hofmann-LaRoche), ARQ-736 (ArQule), DP-4978 (Decihpera) and RAF265 (Novartis).

Vemurafenib is a potent inhibitor of mutant BRAF; particularly of BRAFV600E mutant. Vemurafenib induced complete or partial tumor regression in 81% of patients who had melanoma with the BRAFV600E mutation. Responses were observed at all sites of disease, including the bone, liver, and small bowel. However, after a reliable early response to vemurafenib, responsive tumors were found to develop resistance to treatment. In some patients with BRAFV600E mutations, the tumors showed resistance without evidence of an early response (N. Engl. J. Med., 2010, 363, 9. 809-819). Dabrafenib is a potent and selective RAF kinase inhibitor of human wild type BRAF and CRAF enzymes as well as the mutant forms BRAFV600E, BRAFV600K and BRAFV600D.

MEK1 and MEK2 are dual-specificity kinases that catalyze the phosphorylation of both tyrosine and threonine in target proteins; dual-specificity kinases are included within the protein-serine/threonine kinase family. Protein phosphorylation is the most widespread class of post-translational modification used in signal transduction (Biochemical and Biophysical Research Communications, 2012, 417, 5-10). MEK1 and MEK2 are ubiquitously expressed hydrophilic non-receptor proteins that participate in the RAS-RAF-MEK-ERK signal transduction cascade, which is sometimes denoted as the mitogen activated protein kinase (MAPK) cascade. Ras-mediated Raf activation triggers activation of MEK1 and MEK2 (MAP/ERK kinases 1 and 2), which in turn phosphorylate ERK1 and ERK2 (extracellular signal-regulated kinases 1 and 2) on tyrosine-185 and threonine-183. Activated ERK1 and ERK2 translocate and accumulate in the nucleus, where they can phosphorylate a variety of substrates, including transcription factors that control cellular growth and survival. A controlled regulation of these cascades is involved in cell proliferation and differentiation, whereas an unregulated activation of these kinases can result in oncogenesis. Dysregulation of the RAS/RAF/MEK pathway has been detected in more than 30% of human tumors, however, mutations in the MEK1 and MEK2 genes are seldom, so that hyperactivation of MEK1/2 usually results from gain-of-function mutations in RAS and/or BRAF. Given the importance of the Ras/Raf/MEK/ERK pathway in the development of human cancers, the kinase components of the signal transduction cascade are potentially important targets for the modulation of disease progression in cancer and other proliferative diseases.

A few examples of potent MEK inhibitors include trametinib (Mekinist™), selumetinib (AstraZeneca), binimetinib (Array Biopharma), PD-0325901 (Pfizer), cobimetinib (Exelixis), refametinib (Valeant Pharmaceutical Int.), pimasertib (Santhera Pharmaceuticals), TAK-733 (Takeda) and WX-554 (UCB Pharma S A).

Trametinib is a potent selective inhibitor of MEK1 and MEK2. Significant clinical activity for trametinib is demonstrated in patients with metastatic malignant melanoma with a BRAFV600E or BRAFV600K mutation not previously treated with a BRAF inhibitor when compared to chemotherapy (either dacarbazine or paclitaxel).

Thus, it is evident from the above discussion that metastatic melanoma and resistant BRAF mutant melanoma, continue to be difficult to treat with existing therapies; and therefore, there is a continued need for new effective treatments for these conditions, both, to prevent their progression and to treat the conditions.

SUMMARY OF THE INVENTION

In an aspect, the present invention relates to a pharmaceutical combination comprising a CDK (cyclin dependent kinase) inhibitor represented by a compound of formula I (as described herein) or a pharmaceutically acceptable salt thereof and at least one anticancer agent selected from BRAF (serine-threonine protein kinase B-raf) inhibitor or a MEK (mitogen activated protein kinase) inhibitor, for use in the treatment of melanoma.

In another aspect, the present invention relates to a method of treating melanoma comprising administering to a subject in need thereof; a therapeutically effective amount of a CDK inhibitor represented by a compound of formula I (as described herein) or a pharmaceutically acceptable salt thereof; in combination with a therapeutically effective amount of at least one anticancer agent selected from a BRAF inhibitor or a MEK inhibitor.

In another aspect, the present invention relates to a pharmaceutical composition of the present invention comprising a CDK inhibitor selected from the compounds of formula I or a pharmaceutically acceptable salt thereof and at least one anticancer agent selected from a BRAF inhibitor or a MEK inhibitor, and one or more pharmaceutically acceptable carrier, diluent or excipient.

In a further aspect, the present invention relates to use of a pharmaceutical combination comprising a CDK inhibitor represented by the compound of formula I or a pharmaceutically acceptable salt thereof and at least one anticancer agent selected from a BRAF inhibitor or a MEK inhibitor; for the treatment of melanoma.

In a further aspect, the present invention relates to use of a CDK inhibitor represented by the compound of formula I or a pharmaceutically acceptable salt thereof and at least one anticancer agent selected from a BRAF inhibitor or a MEK inhibitor; for the manufacture of a medicament for the treatment of melanoma.

In a further aspect, the present invention relates to a pharmaceutical kit comprising a CDK inhibitor selected from the compounds of formula I or a pharmaceutically acceptable salt thereof and at least one anticancer agent selected from a BRAF inhibitor or a MEK inhibitor.

Other aspects and further scope of applicability of the present invention will become apparent from the detailed description to follow.

DETAILED DESCRIPTION OF THE INVENTION

Figure 1:
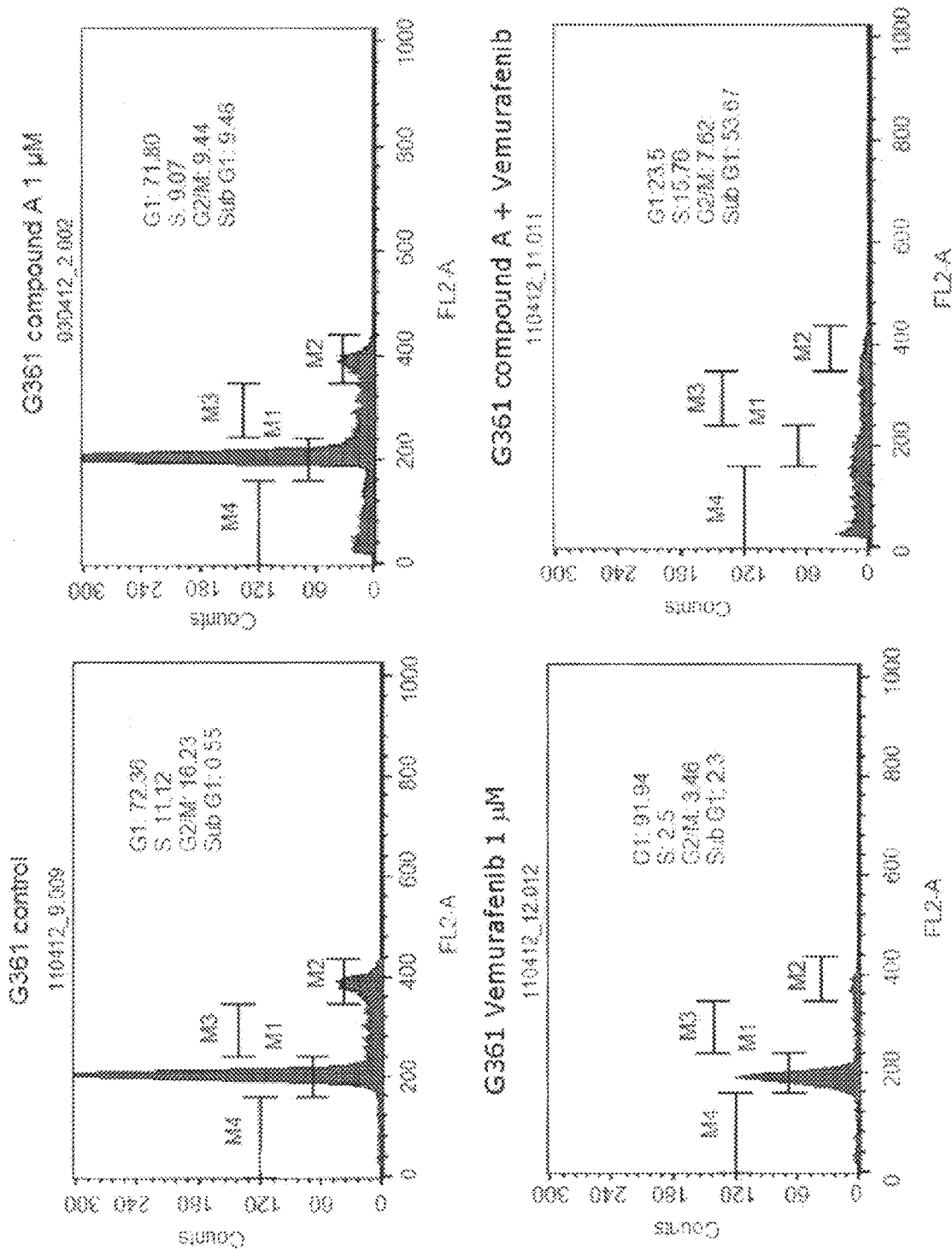
FIG. 1 depicts the effect of compound A (voruciclib) and vemurafenib alone and in combination, on the cell cycle and apoptosis in G361 melanoma cells after 5 days using flow cytometry.

The general terms used hereinbefore and hereinafter preferably have the following meanings within the context of this disclosure, unless otherwise indicated. Thus, the definitions of the general terms as used in the context of the present invention are provided herein below:

The singular forms "a," "an," and "the" include plural reference unless the context clearly dictates otherwise.

Use of "(s)" as part of a term, includes reference to the term singly or in plurality, e.g. the term agent(s) may indicate a single agent or more agents.

As used herein, the term "at least one" is refers to one or more. For instance, the term "at least one anticancer agent" means that the combination comprises a single anticancer agent or more anticancer agents.

It will be understood that "substitution" or "substituted with" includes the implicit proviso that such substitution is in accordance with permitted valence of the substituted atom and the substituent, as well as represents a stable compound, which does not readily undergo transformation such as rearrangement, cyclization, elimination, etc.

As used herein, the term "pharmaceutically acceptable" means that the carrier, diluent, excipients, and/or salt must be compatible with the other ingredients of the formulation, and not deleterious to the recipient thereof. "Pharmaceutically acceptable" also means that the compositions or dosage forms are within the scope of sound medical judgment, suitable for use for an animal or human without excessive toxicity, irritation, allergic response, or other problem or complication, commensurate with a reasonable benefit/risk ratio.

As used herein, the term "combination" or "pharmaceutical combination" means the combined administration of the anticancer agents, in the context of the present invention; a CDK inhibitor (a compound of formula I) and at least one anticancer agent selected from a BRAF inhibitor or a MEK inhibitor; which anticancer agents can be administered independently at the same time or separately within time intervals that especially allow that the combination partners show a synergistic effect.

Cyclin-dependent kinases (CDKs) are a family of enzymes which become activated in specific phases of the cell cycle. CDKs consist of a catalytic subunit (the actual cyclin-dependent kinase or CDK) and a regulatory subunit (cyclin). There are at least nine CDKs (CDK1, CDK2, CDK3, CDK4, CDK5, CDK6, CDK7, CDK8, CDK9, etc.) and at least 15 different types of cyclins (cyclin A, B1, B2, D1, D2, D3, E, H etc.). Each step of the cell cycle is regulated by such CDK complexes: G1/S transition (CDK2/cyclin A, CDK4/cyclin D1-D3, CDK6/cyclin D3), S phase (CDK2/cyclin A), G2 phase 30 (CDK1/cyclin A), G2/M transition phase (CDK1/cyclin B).

As used herein, the term "CDK inhibitor" refers to an agent that is capable of inhibiting one or more cyclin dependent kinase(s) (CDK). Aberrant expression and overexpression of these kinases are evidenced in many disease conditions such as cancer. In the context of the present invention, the CDK inhibitor contained in the pharmaceutical combination of the present invention refers to a compound of formula I or a pharmaceutically acceptable salt thereof. The compounds of the present invention inhibit CDK1/cyclin B, CDK2/cyclin E, CDK4/cyclin D, CDK4/cyclin D1 and/or CDK9/cyclin T1 with specificity.

As used herein, the term "BRAF inhibitor" refers to an agent that is capable of inhibiting BRAF kinase or mutated BRAF kinase activity (one or more mutated forms of serine-threonine protein kinase B-RAF (BRAF)). Ninety percent of reported BRAF mutations result in a substitution of glutamic acid for valine at amino acid 600 (the V600E mutation). Accordingly, the term "BRAF inhibitors" encompasses within its scope a compound that is capable of inhibiting BRAF or its mutated form; or a compound that is capable of inhibiting V600 mutated form of BRAF; or a compound which is capable of inhibiting V600E mutated form of BRAF in both non-refractory and refractory melanoma.

As used herein, the term "MEK inhibitor" refers to an agent that is capable of interacting with a mitogen activated protein kinase (MEK) and inhibiting its enzymatic activity. Inhibiting MEK enzymatic activity in turn reduces the ability of MEK to phosphorylate a substrate peptide or protein. MEK1 and MEK2 are protein kinases that participate in the RAS-RAF-MEK-ERK signal transduction cascade. This cascade participates in the regulation of a large variety of processes including apoptosis, cell cycle progression, cell migration, differentiation, metabolism, and proliferation. Accordingly, the term "MEK inhibitors" encompasses within its scope a compound that is capable of inhibiting MEK.

As used herein, the term "synergistic" or "synergistic effect" or "synergism" as used herein refers to the therapeutic effect of the combination of the compounds (a BRAF inhibitor and a CDK inhibitor, i.e. the compound of formula I), which is greater than the additive effect of the compounds used in the pharmaceutical combination. Advantageously, such synergy between the active ingredients (the therapeutically active compounds) when combined, allows for the use of smaller doses of one or both active ingredients, provides greater efficacy at the same doses, and/or prevents or delays the build-up of multi-drug resistance. The combination index (CI) method of Chou and Talalay can be used to determine the synergy, additive or antagonism effect of the compounds used in combination. When the CI value is less than 1, there is synergy between the compounds used in the combination; when the CI value is equal to 1, there is an additive effect between the compounds used in the combination and when CI value is more than 1, there is an antagonistic effect. The synergistic effect can be attained either by co-formulating the compounds contained in the pharmaceutical combination or the composition of the present invention and administering the said compounds simultaneously through a unit dosage form or as separate formulations administered simultaneously or sequentially.

As used herein, "melanoma" refers to a condition characterized by the growth of a tumor arising from the melanocytic system of the skin and other organs. Most melanocytes occur in the skin, but are also found in the meninges, digestive tract, lymph nodes and eyes. When melanoma occurs in the skin, it is referred to as cutaneous melanoma. Melanoma can also occur in the eyes and is called ocular or intraocular melanoma. Melanoma occurs rarely in the meninges, the digestive tract, lymph nodes or other areas where melanocytes are found.

The terms, "mutant melanoma" or "malignant melanoma" used interchangeably, refers to a melanocytic neoplasm comprising melanoma cells that have a defect (also referred to as a "mutation"). Malignant melanoma usually develops from or near a nevus, consisting of a mass of cells having a marked tendency to metastasis. 40-60% of melanomas carry an activating mutation in the gene encoding the serine-threonine protein kinase B-RAF (BRAF). Among the BRAF mutations observed in melanoma, over 90% are at codon 600, and among these, over 90% are a single nucleotide mutation resulting in substitution of glutamic acid for valine (BRAFV600E). The second most common mutation is BRAFV600K substituting lysine for valine, which represents 5-6% of melanomas, followed by BRAFV600R and BRAFV600D. (Journal of Translational Medicine, 2012, 10, 85, 1-9).

The term "metastatic melanoma" refers to melanoma that has spread through the lymphatic system and/or the blood vessels to other sites of the body including the subcutaneous tissue which lies underneath the skin, the lymph nodes, and to other organs such as the lungs, liver, to bone or to the brain. Stage III melanoma is characterized by the level of lymph node metastasis. There is no evidence of distant metastasis. Stage IV melanoma is characterized by the location of distant metastases and the level of serum lactate dehydrogenase (LDH). This stage is also called as metastatic melanoma.

Unless otherwise indicated, the term "melanoma" can also include recurrent or resistant melanoma. The term "recurrent" or "resistant" refers to the repeated outbreak of melanoma, or a progression of the melanoma independently of whether the disease was cured before said outbreak or progression.

Thus, the treatment of melanoma for which the pharmaceutical combination (as described herein) is provided, refers to treatment of non-refractory, metastatic or refractory (resistant) BRAF mutant melanoma, particularly BRAFV600 mutant melanoma, and more particularly BRAFV600E mutant melanoma.

The term "non-responsive/refractory" as used in reference to melanoma, is used herein to refer to the subjects or patients having melanoma who have been treated with the currently available cancer therapies such as chemotherapy, radiation therapy, surgery, hormonal therapy and/or biological therapy/immunotherapy; for the treatment of melanoma; wherein the therapy is not clinically adequate to treat the patients, such that these patients need additional effective therapy, i.e, remain unsusceptible to therapy. The phrase can also describe subjects or patients who respond to therapy yet suffer from side effects, relapse, develop resistance or do not experience any relief from one or more symptoms of melanoma. In various embodiments, "non-responsive/refractory" means that at least some significant portions of the cancer cells are not killed or their cell division arrested. The determination of whether the cancer cells are "non-responsive/refractory" can be made either in vivo or in vitro by any method known in the art for assaying the effectiveness of treatment on cancer cells, using the art-accepted meanings of "refractory" in such a context.

As used herein the term "treatment cycle" refers to a time period during which a recurring sequence of administration of a CDK inhibitor i.e. the compound of formula I or a pharmaceutically acceptable salt thereof; and at least one anticancer agent selected from a BRAF inhibitor or a MEK inhibitor, is carried out.

The term "apoptosis" refers to the natural process of programmed cell death. It is a process of self-destruction, in which the cell uses specialized cellular machinery to kill itself. The cells disintegrate into membrane-bound particles that are then eliminated by phagocytosis. Apoptosis is a mechanism that enables metazoans to control cell number and eliminate cells that threaten the animal's survival.

The term "subject" as used herein, refers to an animal, preferably a mammal, most preferably a human, who has been the object of treatment, observation or experiment, more particularly a human suffering from melanoma. The term "subject" may be used interchangeably with the term patient. In the context of the present invention the phrase "a subject in need thereof" means a subject in need of the treatment for mutant or malignant melanoma. Alternatively, the phrase "a subject in need thereof" means a subject (patient) diagnosed with mutant or malignant melanoma.

The term "mammal" as used herein is intended to encompass humans, as well as non-human mammals. Non-human mammals include but are not limited to domestic animals, such as cows, pigs, horses, dogs, cats, rabbits, rats and mice, and non-domestic animals.

The term "therapeutically effective amount", as used herein refers to the amount of a CDK inhibitor i.e. the compound of formula I or a pharmaceutically acceptable salt thereof and at least one anticancer agent selected from a BRAF inhibitor or a MEK inhibitor, that, when administered to a subject in need of such treatment, is sufficient to provide therapeutic benefit, that shall include: (i) prevent or delay one or more symptom of melanoma; (ii) ameliorate or eliminate one or more symptom of melanoma; or (iii) treat melanoma.

The term "treat" or "treatment" or "treated" with reference to melanoma in a subject, preferably a mammal, more preferably a human include: (i) inhibition of melanoma i.e., arresting the development of the melanoma; (ii) reduction in the regression of melanoma; (iii) inhibition of tumor cell infiltration into peripheral organs; (iv) inhibition (i.e., reduction, slowing down or complete stopping) of metastasis; (v) amelioration of melanoma, i.e., reducing the severity of the symptoms associated with melanoma; and (vi) relief, to some extent, of one or more symptoms associated with melanoma.

According to one aspect of the present invention, there is provided a pharmaceutical combination comprising a CDK inhibitor selected from a compound of formula I;

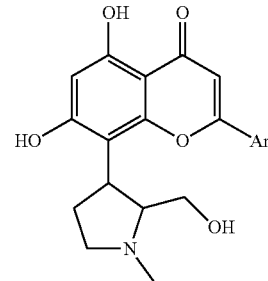

Formula I wherein Ar is a phenyl group, which is substituted by 1 or 2 different substituents selected from chlorine and trifluoromethyl; or a pharmaceutically acceptable salt thereof; and at least one anticancer agent selected from a BRAF inhibitor or a MEK inhibitor; for use in the treatment of melanoma.

According to another embodiment, the CDK inhibitor contained in the pharmaceutical combination of the present invention is selected from a compound of formula I; wherein Ar is a phenyl group substituted by 2 different groups selected from chlorine and trifluoromethyl or a pharmaceutically acceptable salt thereof.

According to another further embodiment, the CDK inhibitor contained in the pharmaceutical combination of the present invention is selected from a compound of formula I wherein Ar is a phenyl group substituted by chlorine; or a pharmaceutically acceptable salt thereof.

The manufacture of the compounds of formula I or the pharmaceutically acceptable salts thereof, and the manufacture of pharmaceutical composition containing the compounds are disclosed in PCT Patent Publication No. WO2004004632 (corresponding to U.S. Pat. No. 7,271,193) and PCT Patent Publication No. WO2007148158. These PCT Patent Publications disclose that the compounds represented by formula I can be used in the treatment of proliferative disorders. As indicated herein above the compounds of formula I may be used in the form of their salts. Preferred salt of compounds of formula I include acetates, alginates, ascorbates, aspartates, benzoates, benzenesulfonates, bisulfates, borates, cinnamates, citrates, ethanesulfonates, fumarates, glucuronates, glutamates, glycolates, hydrochlorides, hydrobromides, hydrofluorides, ketoglutarates, lactates, maleates, malonates, mesylate, nitrates, oxalates, palmoates, perchlorates, phosphates, picrates, salicylates, succinates, sulfamate, sulfates, tartrates, tosylate, trifluoroacetic acid salt and other acid addition salts known to the person skilled in the art.

In one embodiment, the CDK inhibitor (the compound of formula 1) contained in the pharmaceutical combination is (+)-trans-2-(2-chloro-4-trifluoromethylphenyl)-5,7-dihydroxy-8-(2-hydroxymethyl-1-methyl-pyrrolidin-3-yl)-chromen-4-one; or its pharmaceutically acceptable salt.

In another embodiment, the CDK inhibitor (the compound of formula 1) contained in the pharmaceutical combination is (+)-trans-2-(2-chloro-4-trifluoromethyl phenyl)-5,7-dihydroxy-8-(2-hydroxymethyl-1-methyl pyrrolidin-3- yl)-chromen-4-one hydrochloride (referred to herein as "compound A". Compound A is also referred to herein as "voruciclib").

In one embodiment, the CDK inhibitor (compound of formula 1) contained in the pharmaceutical combination is (+)-trans-2-(2-chloro-phenyl)-5,7-dihydroxy-8-(2-hydroxymethyl-1-methyl-pyrrolidin-3-yl)-chromen-4-one or its pharmaceutically acceptable salt.

In another embodiment, the CDK inhibitor (compound of formula 1) contained in the pharmaceutical combination is (+)-trans-2-(2-chloro-phenyl)-5,7-dihydroxy-8-(2-hydroxymethyl-1-methyl-pyrrolidin-3-yl)-chromen-4-one hydrochloride (referred to herein as "compound B". Compound B is also referred to herein as "riviciclib").

In an embodiment, the BRAF inhibitor contained in the pharmaceutical combination is an inhibitor of V600 mutated form of BRAF.

In an embodiment, the BRAF inhibitor contained in the pharmaceutical combination is an inhibitor of V600E mutated form of BRAF.

In an embodiment, the BRAF inhibitor contained in the pharmaceutical combination is selected from BAY43-9006 (sorafenib, Bayer), vemurafenib (PLX4032, Plexxikon; RG7204, RO5185426, Hofmann-LaRoche), GDC-0879 (GlaxoSmithKline), dabrafenib (GSK2118436, GlaxoSmithKline), PLX4720 (Hofmann-LaRoche), BMS-908662 (XL281, Bristol-Myers Squibb), LGX818 (Novartis), PLX3603 (RO5212054, Hofmann-LaRoche), ARQ-736 (ArQule), DP-4978 (Deciphera) or RAF265 (Novartis).

In an embodiment, the BRAF inhibitor contained in the pharmaceutical combination is vemurafenib.

In an embodiment, the BRAF inhibitor contained in the pharmaceutical combination is dabrafenib.

In an embodiment, the MEK inhibitor contained in the pharmaceutical combination is an inhibitor of V600 mutated form of BRAF.

In an embodiment, the MEK inhibitor contained in the pharmaceutical combination is an inhibitor of V600E or V600K mutated form of BRAF.

In an embodiment, the MEK inhibitor contained in the pharmaceutical combination is selected from selumetinib (AstraZeneca), binimetinib (Array Biopharma), PD-0325901 (Pfizer), trametinib (Mekinist™), cobimetinib (Exelixis), refametinib (Valeant), pimasertib (Santhera Pharmaceuticals), TAK-733 (Takeda) or WX-554 (UCB Pharma S A).

In an embodiment, the MEK inhibitor contained in the pharmaceutical combination is trametinib.

In an embodiment, the present invention relates to a pharmaceutical combination for use in the treatment of melanoma, wherein said pharmaceutical combination comprises a therapeutically effective amount of a CDK inhibitor selected from the compound of formula I or a pharmaceutically acceptable salt thereof; and a therapeutically effective amount of at least one anticancer agent selected from a BRAF inhibitor and a MEK inhibitor, wherein said CDK inhibitor and at least one of the said anticancer agents; are administered simultaneously.

In an embodiment, the present invention relates to a pharmaceutical combination for use in the treatment of melanoma, wherein said pharmaceutical combination comprises a therapeutically effective amount of a CDK inhibitor selected from the compound of formula I or a pharmaceutically acceptable salt thereof and a therapeutically effective amount of at least one anticancer agent selected from a BRAF inhibitor and a MEK inhibitor, wherein said CDK inhibitor and at least one of the said anticancer agents; are administered sequentially.

In an embodiment, the present invention relates to a pharmaceutical combination for use in the treatment of melanoma, wherein said pharmaceutical combination comprises a therapeutically effective amount of a CDK inhibitor selected from the compound of formula I or a pharmaceutically acceptable salt thereof; and a therapeutically effectively amount of at least one anticancer agent selected from a BRAF inhibitor or a MEK inhibitor, wherein the said anticancer agent is administered prior to the administration of the CDK inhibitor.

In an embodiment, the present invention relates to a pharmaceutical combination for use in the treatment of melanoma, wherein said pharmaceutical combination comprises a therapeutically effective amount of a CDK inhibitor selected from the compound of formula I or a pharmaceutically acceptable salt thereof; and a therapeutically effectively amount of at least one anticancer agent selected from a BRAF inhibitor or a MEK inhibitor, wherein the CDK inhibitor is administered prior to the administration of the said anticancer agent.

In one embodiment, the present invention relates to a pharmaceutical combination for use in the treatment of melanoma, wherein said pharmaceutical combination comprises a therapeutically effective amount of a CDK inhibitor selected from the compound of formula I or a pharmaceutically acceptable salt thereof; and a therapeutically effectively amount of at least one anticancer agent selected from a BRAF inhibitor or a MEK inhibitor, wherein the CDK inhibitor and the said anticancer agent are both administered once a day.

In another embodiment, the present invention relates to a pharmaceutical combination for use in the treatment of melanoma, wherein said pharmaceutical combination comprises a therapeutically effective amount of a CDK inhibitor selected from the compound of formula I or a pharmaceutically acceptable salt thereof and a therapeutically effectively amount of at least one anticancer agent selected from a BRAF inhibitor or a MEK inhibitor, wherein the CDK inhibitor is administered once a day, while the said anticancer agent is administered twice a day.

In yet another embodiment, the present invention relates to a pharmaceutical combination for use in the treatment of melanoma, wherein said pharmaceutical combination comprises a therapeutically effective amount of a CDK inhibitor selected from the compound of formula I or a pharmaceutically acceptable salt thereof; and a therapeutically effectively amount of at least one anticancer agent selected from a BRAF inhibitor or a MEK inhibitor, wherein the CDK inhibitor and the said anticancer agent are both administered twice a day.

In one aspect, the present invention relates to a method for the treatment of melanoma comprising administering to a subject in need thereof; a therapeutically effective amount of a CDK inhibitor selected from the compound of formula I (as described herein) or a pharmaceutically acceptable salt thereof; and a therapeutically effective amount of at least one anticancer agent selected from a BRAF inhibitor or a MEK inhibitor.

In an embodiment, the present invention relates to a method of treating melanoma comprising administering to a subject in need thereof; a therapeutically effective amount of a CDK inhibitor selected from the compound of formula I or a pharmaceutically acceptable salt thereof; and a therapeutically effective amount of at least one anticancer agent selected from a BRAF inhibitor or a MEK inhibitor, wherein the CDK inhibitor and the said anticancer agent are administered simultaneously.

In an embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of at least one anticancer agent selected from a BRAF inhibitor or a MEK inhibitor, wherein the CDK inhibitor and the said anticancer agent are administered sequentially.

In an embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of at least one anticancer agent selected from a BRAF inhibitor or a MEK inhibitor, wherein the said anticancer agent is administered prior to the administration of the said CDK inhibitor.

In an embodiment, the present invention relates to a method of treating melanoma comprising administering to a subject in need thereof a therapeutically effective amount of the CDK inhibitor selected from the compound of formula I or a pharmaceutically acceptable salt thereof; and a therapeutically effective amount of at least one anticancer agent selected from a BRAF inhibitor or a MEK inhibitor, wherein the said CDK inhibitor is administered prior to the administration of said anticancer agent.

In one embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of at least one anticancer agent selected from a BRAF inhibitor or a MEK inhibitor, wherein the said CDK inhibitor and the said anticancer agent are both administered once a day.

In another embodiment, the present invention relates to a method of treating melanoma comprising administering to a subject in need thereof a therapeutically effective amount of a CDK inhibitor selected from the compound of formula I or a pharmaceutically acceptable salt thereof and a therapeutically effective amount of at least one of a BRAF inhibitor or a MEK inhibitor, wherein the said CDK inhibitor is administered once a day and the said anticancer agent is administered twice a day.

In yet another embodiment, the present invention relates to a method of treating melanoma comprising administering to a subject in need thereof a therapeutically effective amount of a CDK inhibitor selected from the compound of formula I or a pharmaceutically acceptable salt thereof and a therapeutically effective amount of at least one of a BRAF inhibitor or a MEK inhibitor, wherein the said CDK inhibitor and the said anticancer agent are both administered twice a day.

In an embodiment, the method of treating melanoma comprises administering to the subject in need thereof; the CDK inhibitor selected from the compound of formula I and at least one anticancer agent selected from a BRAF inhibitor or a MEK inhibitor in the dose range described herein.

In an embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effective amount of a BRAF inhibitor, wherein the said BRAF inhibitor and said CDK inhibitor are administered simultaneously.

In an embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effective amount of a BRAF inhibitor, wherein the said BRAF inhibitor and the said CDK inhibitor are administered sequentially.

In an embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effectively amount of a BRAF inhibitor, wherein the said BRAF inhibitor is administered prior to the administration of the said CDK inhibitor.

In an embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effectively amount of a BRAF inhibitor, wherein the said CDK inhibitor is administered prior to the administration of the said BRAF inhibitor.

In one embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effectively amount of a BRAF inhibitor, wherein the said CDK inhibitor and the said BRAF inhibitor are both administered once a day.

In another embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effectively amount of a BRAF inhibitor, wherein the said CDK inhibitor is administered once a day and the said BRAF inhibitor is administered twice a day.

In yet another embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effectively amount of a BRAF inhibitor, wherein the said CDK inhibitor and the said BRAF inhibitor are both administered twice a day.

In one aspect, the present invention relates to a method for the treatment of melanoma comprising administering to a subject in need thereof a therapeutically effective amount of a CDK inhibitor selected from the compound of formula I (as described herein) or a pharmaceutically acceptable salt thereof and a BRAF inhibitor.

In an embodiment, the present invention relates to a method of treating melanoma comprising administering to a subject in need thereof a therapeutically effective amount of a CDK inhibitor selected from the compound of formula I or a pharmaceutically acceptable salt thereof and a therapeutically effective amount of a BRAF inhibitor, wherein the said BRAF inhibitor and the said CDK inhibitor are administered simultaneously.

In an embodiment, the present invention relates to a method of treating melanoma comprising administering to a subject in need thereof a therapeutically effective amount of a CDK inhibitor selected from the compound of formula I or a pharmaceutically acceptable salt thereof and a therapeutically effective amount of a BRAF inhibitor, wherein the said BRAF inhibitor and the said CDK inhibitor are administered sequentially.

In an embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of a BRAF inhibitor, wherein the said BRAF inhibitor is administered prior to the administration of the said CDK inhibitor.

In an embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of a BRAF inhibitor, wherein the said CDK inhibitor is administered prior to the administration of the said BRAF inhibitor.

In one embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of a BRAF inhibitor, wherein the said CDK inhibitor and the said BRAF inhibitor are both administered once a day.

In another embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of a BRAF inhibitor, wherein the said CDK inhibitor is administered once a day, while the said BRAF inhibitor is administered twice a day.

In yet another embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of a BRAF inhibitor, wherein the said CDK inhibitor and the said BRAF inhibitor are both administered twice a day.

In an embodiment, the method of treating melanoma comprises administering to the subject in need thereof; the BRAF inhibitor and the CDK inhibitor selected from the compound of formula I or a pharmaceutically acceptable salt thereof; in the dose range described herein.

In an embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effective amount of a MEK inhibitor, wherein the said MEK inhibitor and the said CDK inhibitor are administered simultaneously.

In an embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effective amount of a MEK inhibitor, wherein the MEK inhibitor and the CDK inhibitor are administered sequentially.

In an embodiment, the present invention relates to a pharmaceutical combination for use in the treatment of melanoma, wherein said pharmaceutical combination comprises a therapeutically effective amount of a CDK inhibitor selected from the compound of formula I or a pharmaceutically acceptable salt thereof; and a therapeutically effectively amount of a MEK inhibitor, wherein the said MEK inhibitor is administered prior to the administration of the said CDK inhibitor.

In an embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effectively amount of a MEK inhibitor, wherein the said CDK inhibitor is administered prior to the administration of the said MEK inhibitor.

In one embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effectively amount of a MEK inhibitor, wherein the said CDK inhibitor and the said MEK inhibitor are both administered once a day.

In another embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof; and a therapeutically effectively amount of a MEK inhibitor, wherein the said CDK inhibitor is administered once a day, while the said MEK inhibitor is administered twice a day.

In yet another embodiment, the present invention relates to a pharmaceutical combination for use in the treatment of melanoma, wherein the said pharmaceutical combination comprises a therapeutically effective amount of a CDK inhibitor selected from the compound of formula I or a pharmaceutically acceptable salt thereof and a therapeutically effectively amount of a MEK inhibitor, wherein the said CDK inhibitor and the said MEK inhibitor are both administered twice a day.

In one aspect, the present invention relates to a method for the treatment of melanoma comprising administering to a subject in need thereof a therapeutically effective amount of a CDK inhibitor selected from the compound of formula I (as described herein) or a pharmaceutically acceptable salt thereof and a MEK inhibitor.

In an embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of a MEK inhibitor, wherein the said MEK inhibitor and the said CDK inhibitor are administered simultaneously.

In an embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of a MEK inhibitor, wherein the said MEK inhibitor and the said CDK inhibitor are administered sequentially.

In an embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of a MEK inhibitor, wherein the said MEK inhibitor is administered prior to the administration of the said CDK inhibitor.

In an embodiment, the present invention relates to a method of treating melanoma comprising administering to a subject in need thereof a therapeutically effective amount of the CDK inhibitor selected from the compound of formula I or a pharmaceutically acceptable salt thereof; and a therapeutically effective amount of a MEK inhibitor, wherein the said CDK inhibitor is administered prior to the administration of the said MEK inhibitor.

In one embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of a MEK inhibitor, wherein the said CDK inhibitor and the said MEK inhibitor are both administered once a day.

In another embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of a MEK inhibitor, wherein the said CDK inhibitor is administered once a day, while the said MEK inhibitor is administered twice a day.

In yet another embodiment, the present invention relates to a method of treating melanoma comprising administering to a subject in need thereof a therapeutically effective amount of a CDK inhibitor selected from the compound of formula I or a pharmaceutically acceptable salt thereof; and a therapeutically effective amount of a MEK inhibitor, wherein the said CDK inhibitor and the said MEK inhibitor are both administered twice a day.

In an embodiment, the method of treating melanoma comprises administering to the subject in need thereof; the MEK inhibitor and the CDK inhibitor selected from the compound of formula I or a pharmaceutically acceptable salt thereof; in the dose range described herein.

In an embodiment, the present invention relates to a pharmaceutical combination for use in the treatment of melanoma, wherein said pharmaceutical combination comprises a therapeutically effective amount of a CDK inhibitor selected from the compound of formula I or a pharmaceutically acceptable salt thereof; a therapeutically effective amount of a BRAF inhibitor and a therapeutically effective amount of a MEK inhibitor.

In an embodiment, the present invention relates to a method of treating melanoma comprising administering to a subject in need thereof a therapeutically effective amount of a CDK inhibitor selected from the compound of formula I or a pharmaceutically acceptable salt thereof; a therapeutically effective amount of a BRAF inhibitor and a therapeutically effective amount of a MEK inhibitor.

In one embodiment of the present invention, the melanoma being treated is non-refractory melanoma.

In another embodiment of the present invention, the melanoma being treated is non-refractory BRAF mutant melanoma.

In yet another embodiment of the present invention, the melanoma being treated is non-refractory BRAF V600 mutant melanoma.

In a further embodiment of the present invention, the melanoma being treated is non-refractory BRAF V600E or BRAF V600K mutant melanoma.

In one embodiment of the present invention, the melanoma being treated is recurrent or refractory melanoma.

In another embodiment of the present invention, the melanoma being treated is resistant BRAF mutant melanoma.

In yet another embodiment of the present invention, the melanoma being treated is resistant BRAF V600 mutant melanoma.

In a further embodiment of the present invention, the melanoma being treated is resistant BRAF V600E or BRAF V600K mutant melanoma.

In one embodiment of the present invention, the melanoma being treated is metastatic melanoma.

In another embodiment of the present invention, the melanoma being treated is metastatic BRAF mutant melanoma.

In yet another embodiment of the present invention, the melanoma being treated is metastatic BRAFV600 mutant melanoma.

In a further embodiment of the present invention, the melanoma being treated is metastatic BRAFV600E or BRAFV600K mutant melanoma.

According to the present invention, administration of the CDK inhibitors (the compound of formula I) and/or anti-cancer agent selected from a BRAF inhibitor and/or a MEK inhibitor can be by any suitable route, including, without limitation, parenteral, oral, sublingual, transdermal, topical, intranasal, aerosol, intraocular, intratracheal or intrarectal.

In one embodiment, the CDK inhibitor can be administered orally to generate and maintain good blood levels thereof, while the anticancer agent(s) selected from a BRAF inhibitor and/or a MEK inhibitor can be administered parenterally, by intravenous, subcutaneous, intramuscular, intravascular or infusion route.

In another embodiment, the CDK inhibitor can be administered parenterally by intravenous, subcutaneous, intramuscular, intravascular or infusion route, while the anticancer agent(s) selected from a BRAF inhibitor and/or a MEK inhibitor can be administered orally.

In a further embodiment, both, the CDK inhibitor and the anticancer agent(s) selected from a BRAF inhibitor and/or a MEK inhibitor can be administered orally to generate and maintain good blood levels thereof.

In a still further embodiment, both the CDK inhibitor of formula I and the anticancer agent(s) selected from a BRAF inhibitor and/or a MEK inhibitor can be administered parenterally by intravenous, subcutaneous, intramuscular intravascular or infusion route, to generate and maintain good blood levels thereof.

In an aspect, the present invention relates to a pharmaceutical composition for use in the treatment of melanoma, wherein the said composition comprises a CDK inhibitor selected from the compounds of formula I or pharmaceutically acceptable salts thereof; and at least one anticancer agent selected from a BRAF inhibitor or a MEK inhibitor and one or more pharmaceutically acceptable carrier, diluent, or excipient. For the production of pills, tablets, coated tablets and hard gelatin capsules, the pharmaceutically active excipients that can be used include, but not limited to, lactose, corn starch or derivatives thereof, gum arabica, magnesia or glucose, etc. For soft gelatin capsules and suppositories, the carriers that can be used include, but not limited to, fats, waxes, natural or hardened oils, etc. Suitable carriers for the production of solutions, are, for example injection solutions, or for emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

The CDK inhibitor (the compound of formula I) and the anticancer agent(s) selected from a BRAF inhibitor and/or a MEK inhibitor can be formulated singly or in combination into pharmaceutical dosage forms using conventional pharmaceutical techniques familiar to one skilled in the art such as by means of blending, granulating, dissolving or lyophilizing.

In general, compositions intended for pharmaceutical use may be prepared according to any method known in the art for the manufacture of pharmaceutical compositions, e.g. *Remington—The Science and Practice of Pharmacy* ($21^{st}$ *Edition*) (2005), *Goodman & Gilman's The Pharmacological Basis of Therapeutics* ($11^{th}$ *Edition*) (2006) and *Ansel's Pharmaceutical Dosage Forms and Drug Delivery Systems* ($9^{th}$ *Edition*), and *Solid-State Chemistry of Drugs* ($2^{nd}$ *Edition*) (1999).

The compositions described herein can be in a form suitable for oral administration, for example, solid dosage forms such as tablets, capsules, lozenges, or granules; liquid dosage forms such as, emulsions, solutions, suspensions; for parenteral injection (including intravenous, subcutaneous, intramuscular, intravascular or infusion) for example as a sterile solution, suspension or emulsion; for topical administration for example as an ointment, cream, gel or lotion.

Compositions for oral administrations can be in the form of tablets, lozenges, aqueous or oily suspensions, granules, powders, cachets, emulsions, capsules, syrups, or elixirs. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Selectively permeable membranes surrounding an osmotically active driving compound are also suitable for oral administration of the compounds (the CDK inhibitor, and/or the anticancer agent(s) selected from a BRAF inhibitor and/or a MEK inhibitor) contained in the pharmaceutical combination according to the present invention. Compositions suitable for oral administration can include standard vehicles such as mannitol, lactose, starch, corn starch, magnesium stearate, talc, sodium saccharine, cellulose, magnesium carbonate, etc. Such vehicles are preferably of pharmaceutical grade.

For ointments, creams, the active ingredient (CDK inhibitor and/or anticancer agent(s) selected from a BRAF inhibitor and/or a MEK inhibitor) is formulated in oil-in-water or water-in-oil base.

For intramuscular, intraperitoneal, subcutaneous and intravenous use, sterile solutions of the active ingredient (CDK inhibitor and/or anticancer agent(s) selected from a BRAF inhibitor and/or a MEK inhibitor) are usually employed, and the pH of the solutions should be suitably adjusted and buffered.

Further, the effect of the compounds i.e. the CDK inhibitors and/or anticancer agent(s) selected from a BRAF inhibitor and/or a MEK inhibitor contained in the pharmaceutical composition can be delayed or prolonged through a proper formulation. For example, a slowly soluble pellet of the compound may be prepared and incorporated in a tablet or capsule. The technique can be improved by making pellets of several different dissolution rates and filling capsules with a mixture of the pellets. Tablets or capsules can be coated with a film which resists dissolution for a predictable period of time. Even the parenteral preparations can be made long-acting, by dissolving or suspending the compound in oily or emulsified vehicles which allow it to disperse only slowly in the serum.

Although the effective doses of the CDK inhibitor selected from the compounds of formula I and the anticancer agent(s) selected from a BRAF inhibitor and/or a MEK inhibitor) used for administration vary depending on the severity of the disease (melanoma), the severity of symptoms, the age, sex, body weight and sensitivity difference of the patient, the mode, time, interval and duration of administration, the nature and type of formulation, etc. In certain embodiments, the therapeutic agents contained in the pharmaceutical combination according to the present invention are administered in a time frame where both the agents are still active. One skilled in the art would be able to determine such a time frame by determining the half life of the administered the said therapeutic agents. As indicated herein before, the anticancer agents contained in the pharmaceutical composition can be administered simultaneously or sequentially. Those skilled in the art will recognize that several variations are possible within the scope and spirit of this invention.

The dosage of the therapeutic agents to be administered should be selected to produce the desired effect. A suitable dosage of the CDK inhibitor can be from about 5 mg to about 500 mg. The dose of the CDK inhibitor, which is to be administered, can cover a wide range depending on the severity of the melanoma to be treated. The dose to be administered daily can be selected to obtain the desired effect. A suitable dose can range from about 50 mg/day to 350 mg/day of the CDK inhibitor. If required, higher or lower daily doses can also be administered.

In an embodiment, the BRAF inhibitor can be administered from about 1 mg/day to about 2500 mg/day and this amount can be given in a single or multiple doses per day or per dose or per cycle of treatment.

In an embodiment, the MEK inhibitor can be administered from about 0.01 mg/day to 2000 mg/day and this amount can be given in a single or multiple doses per day or per dose or per cycle of treatment.

In an embodiment, the CDK inhibitor and the anticancer agent(s) selected from a BRAF inhibitor and/or a MEK inhibitor are both administered once a day. In another embodiment, the CDK inhibitor and the anticancer agent(s) selected from a BRAF inhibitor and/or a MEK inhibitor are both administered twice a day. In a further embodiment, the CDK inhibitor is administered once a day, while the anticancer agent(s) selected from a BRAF inhibitor and/or a MEK inhibitor is administered twice a day. However, the amount of each therapeutic agent contained in the pharmaceutical combination according to the present invention, when used in combination will typically be less than an amount that would produce a therapeutic effect if administered alone. For convenience, the total daily dose can be divided and administered in portions during the day if desired.

The combinations provided by this invention have been evaluated in certain assay systems, and in several different administrative schedules in vitro. The experimental details are as provided herein below. The data presented herein clearly indicate that the BRAF inhibitor or the MEK inhibitor when combined with a CDK inhibitor selected from the compounds of formula I or a pharmaceutically acceptable salt thereof exhibit synergistic effect. It is clearly indicated that the therapeutic agents when used in combination in the treatment of melanoma increases apoptosis or cytotoxicity in proliferative cells than when the cells are treated with only the CDK inhibitor (i.e. the compound of formula I or its pharmaceutically acceptable salt, alone) or only the BRAF inhibitor or only the MEK inhibitor.

In an aspect, the present invention relates to a pharmaceutical kit comprising a CDK inhibitor (the compound of formula I or a pharmaceutically acceptable salt thereof) and at least one anticancer agent selected from a BRAF inhibitor or a MEK inhibitor. The pharmaceutical kit may comprise a container containing a compound of formula I or a pharmaceutically acceptable salt thereof and at least one anticancer agent selected from a BRAF inhibitor or a MEK inhibitor as a fixed dose formulation; or the kit may comprise two or more separate containers for the compound of formula I or a pharmaceutically acceptable salt thereof; and at least one anticancer agent selected from a BRAF inhibitor or a MEK inhibitor. The kit may further comprise a package insert, including information about the indication, usage, doses, direction for administration, contraindications, precautions and warnings. The suitable container that can be used includes a bottle, a vial, an ampoule, a syringe or a blister pack. The pharmaceutical kit may optionally comprise a further container comprising a pharmaceutically acceptable buffer, water for injection, phosphate-buffered saline, Ringer's solution and dextrose solution.

The CDK inhibitors i.e. the compounds of formula I contained in the pharmaceutical combination of the present invention; may be prepared according to the methods disclosed in PCT Patent Publication No. WO2004004632 and PCT Patent Publication No. WO2007148158.

The general process for the preparation of compounds of formula I, or a pharmaceutically acceptable salt thereof, comprises the following steps:

(a) treating the resolved enantiomerically pure (–)-trans enantiomer of the intermediate compound of formula VIA,

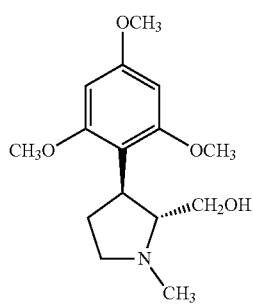

with acetic anhydride in the presence of a Lewis acid catalyst to obtain a resolved acetylated compound of formula VIIA,

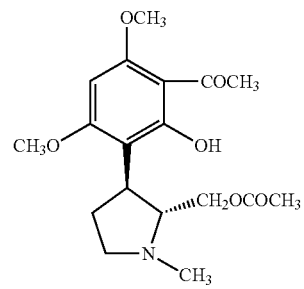

(b) reacting the resolved acetylated compound of formula VIIA with an acid of formula ArCOOH or an acid chloride of formula ArCOCl or an acid anhydride of formula $(ArCO)_2O$ or an ester of formula $ArCOOCH_3$, wherein Ar is as defined hereinabove in reference to the compound of formula I, in the presence of a base and a solvent to obtain a resolved compound of formula VIIIA;

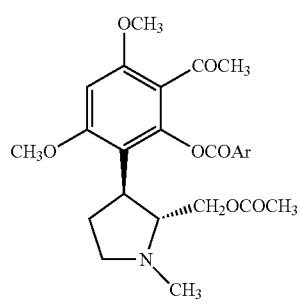

(c) treating the resolved compound of formula VIIIA with a base in a suitable solvent to obtain the corresponding resolved β-diketone compound of formula IXA;

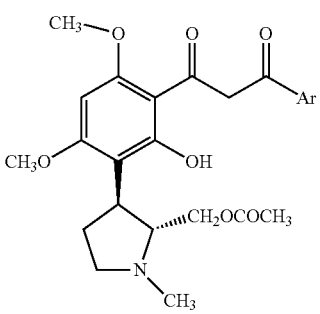

wherein Ar is as defined above;

(d) treating the resolved β-diketone compound of formula IXA with an acid such as hydrochloric acid to obtain the corresponding cyclized compound of formula XA,

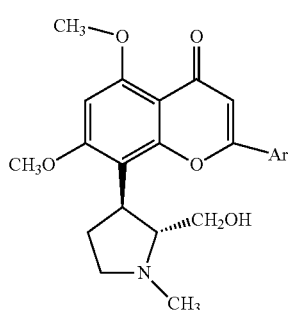

(e) subjecting the compound of formula XA to dealkylation by heating it with a dealkylating agent at a temperature ranging from 120-180° C. to obtain the (+)-trans enantiomer of the compound of formula I and, optionally, converting the subject compound into its pharmaceutically acceptable salt.

The Lewis acid catalyst utilized in the step (a) above may be selected from: $BF_3$, $Et_2O$, zinc chloride, aluminium chloride and titanium chloride.

The base utilized in the process step (b) may be selected from triethylamine, pyridine and a DCC-DMAP combination (combination of N,N'-dicyclohexyl carbodiimide and 4-dimethylaminopyridine).

It will be apparent to those skilled in the art that the rearrangement of the compound of formula VIIIA to the corresponding β-diketone compound of formula IXA is known as a Baker-Venkataraman rearrangement (*J. Chem. Soc.*, 1933, 1381 and *Curr. Sci.*, 1933, 4, 214).

The base used in the process step (c) may be selected from: lithium hexamethyl disilazide, sodium hexamethyldisilazide, potassium hexamethyldisilazide, sodium hydride and potassium hydride. A preferred base is lithium hexamethyl disilazide.

The dealkylating agent used in process step (e) for the dealkylation of the compound of formula IXA may be selected from: pyridine hydrochloride, boron tribromide, boron trifluoride etherate and aluminium trichloride. A preferred dealkylating agent is pyridine hydrochloride.

Preparation of the starting compound of formula VIA involves reacting 1-methyl-4-piperidone with a solution of 1,3,5-trimethoxybenzene in glacial acetic acid, to yield 1-methyl-4-(2,4,6-trimethoxyphenyl)-1,2,3,6-tetrahydropyridine, which is reacted with boron trifluoride diethyl etherate, sodium borohydride and tetrahydrofuran to yield 1-methyl-4-(2,4,6-trimethoxyphenyl)piperidin-3-ol. Conversion of 1-methyl-4-(2,4,6-trimethoxyphenyl)piperidin-3-ol to the compound of formula VIA involves converting the hydroxyl group present on the piperidine ring of the compound, 1-methyl-4-(2,4,6-trimethoxyphenyl) piperidin-3-ol to a leaving group such as tosyl, mesyl, triflate or halide by treatment with an appropriate reagent such as p-toluenesulfonylchloride, methanesulfonylchloride, triflic anhydride or phosphorous pentachloride in the presence of oxygen nucleophiles such as triethylamine, pyridine, potassium carbonate or sodium carbonate, followed by ring contraction in the presence of oxygen nucleophiles such as sodium acetate or potassium acetate in an alcoholic solvent such as isopropanol, ethanol or propanol.

The representative compound, compound A (also referred to as voruciclib) used in the pharmacological assays refers to (+)-trans-2-(2-chloro-4-trifuorophenyl)-5,7-dihydroxy-8-(2-hydroxymethyl-1-methyl-pyrrolidin-3-yl)-chromen-4-one hydrochloride and was one of the compounds disclosed in the published PCT Publication No. WO2007148158.

Another representative compound, the compound B (also referred to as riviciclib) used in the pharmacological assays refers to (+)-trans-2-(2-chlorophenyl)-5,7-dihydroxy-8-(2-hydroxymethyl-1-methyl-pyrrolidin-3-yl)-chromen-4-one hydrochloride and was one of the compounds disclosed in published PCT Publication No. WO2004004632.

The synergistic effect of the combination according to the present invention comprising the CDK inhibitor and at least one anticancer agent selected from a BRAF inhibitor or a MEK inhibitor is now explained in more detail with reference to preferred embodiments thereof. It is to be noted that these are provided only as examples and not intended to limit the invention.

It is to be understood that the invention may assume various alternative variations and step sequences, except where expressly specified to the contrary. Moreover, other than any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims may vary depending upon the desired properties to be obtained by the present invention.

Those skilled in the art will recognize that several variations are possible within the scope and spirit of this invention. The invention will now be described in greater detail by reference to the following non-limiting examples. The following examples further illustrate the invention but, of course, should not be construed as in any way limiting its scope.

EXAMPLES

The following abbreviations or terms are used herein:
$BF_3$: Boron trifluoride
$BF_3 \cdot Et_2O$: Boron trifluoride diethyl etherate
$CaCl_2$: Calcium chloride
$CHCl_3$: Chloroform
$CDCl_3$: Deuteriated chloroform
$CO_2$: Carbon dioxide
DCC: N,N'-dicyclohexyl carbodiimide
DMAP: 4-Dimethylaminopyridine
DMF: N,N-dimethylformamide
DMSO: Dimethylsulfoxide
$Et_2O$: Diethyl ether
EtOAc: Ethyl acetate
g: Gram
h: Hour
HCl: Hydrochloric acid
IPA: Isopropyl alcohol
KBr: Potassium bromide
Kg: Kilogram
L: Litre
MeOH: Methanol
min: Minute(s)
mg: Milligram
mL: Millilitre
μL: Microlitre
μM: Micromolar
mmol: Millimolar
mol: Mole
NaCl: Sodium chloride
$Na_2CO_3$: Sodium carbonate
$NaHCO_3$: Sodium bicarbonate Na$_2$SO$_4$: Sodium sulfate
n-BuLi: n-Butyl Lithium
PEL: Piramal Enterprises Limited
° C.: Degree Centigrade
THF: Tetrahydrofuran

EXAMPLES

Preparation of the Compound A (Voruciclib) and the Compound B (Riviciclib), the Representative Compounds of Formula 1 are Presented Herein as Reference Examples:

Reference Example 1

(a) Preparation of (+)-trans-2-(2-chloro-4-trifluoromethylphenyl)-8-(2-hydroxy methyl-1-methyl pyrrolidin-3-yl)-5,7-dimethoxy-chromen-4-one To a solution of n-BuLi (15% solution in hexane, 2.2 mL, 5 mmol) in THF (10 mL), maintained at 0° C. under nitrogen atmosphere, hexamethyldisilazane (1.08 mL, 5.1 mmol) was added dropwise and stirred for 15 min. To this, a solution of (+)-trans-2-chloro-4-trifluoromethylbenzoic acid 2-(2-acetoxymethyl-1-methyl-pyrrolidin-3-yl)-6-acetyl-3,5-dimethoxyphenyl ester (1.44 g, 2.5 mmol) in THF (10 mL) was added dropwise, maintaining the temperature at 0° C. After the addition, the reaction was allowed to warm to room temperature and stirred for 2.5 h. The reaction mixture was acidified with dilute HCl, and basified with 10% sodium bicarbonate to pH 8 to 9. The aqueous layer was extracted with chloroform (3×25 mL). The organic layer was washed with water (25 mL), brine (25 mL) and dried over anhydrous Na$_2$SO$_4$. The organic layer was concentrated under reduced pressure and dried under vacuum to yield acetic acid 3-{3-[3-(2-chloro-4-trifluromethyl-phenyl)-3-oxo-propionyl]-2-hydroxy-4,6-dimethoxy-phenyl}-1-methyl-pyrrolidin-2-yl-methyl ester as an oil (1.3 g, 90.2%). This ester was dissolved in concentrated HCl (10 mL) and stirred for 3 h to effect cyclization. At the end of 3 h, the reaction mixture was basified with solid NaHCO$_3$ to pH 8 to 9. The aqueous layer was extracted with chloroform (25×3 mL) and washed with water (25 mL) and brine (25 mL). The organic layer was dried over anhydrous Na$_2$SO$_4$, concentrated under reduced pressure and dried over vacuum. The residue was purified by column chromatography with 3% methanol in chloroform and 0.1% ammonia as eluent to yield the compound, (+)-trans-2-(2-chloro-4-trifluoromethylphenyl)-8-(2-hydroxymethyl-1-methylpyrrolidin-3-yl)-5,7-dimethoxy-chromen-4-one as a yellow solid.

Yield: 0.56 g (48.2%); $^1$H NMR (CDCl$_3$, 300 MHz): δ 7.95 (d, 1H), 7.78 (s, 1H), 7.69 (d, 1H), 6.61 (s, 1H), 6.46 (s, 1H), 4.21 (m, 1H), 4.01 (s, 3H), 3.93 (s, 3H), 3.71 (dd, 1H), 3.41 (d, 1H), 3.26 (m, 1H), 2.84 (m, 1H), 2.70 (m, 1H), 2.44 (s, 3H), 2.10 (m, 2H); MS (ES+): m/z 497 (M+1).

(b) Preparation of (+)-trans-2-(2-chloro-4-trifluoromethyl-phenyl)-5,7-dihydroxy-8-(2-hydroxymethyl-1-methylpyrrolidin-3-yl)-chromen-4-one A mixture of the compound as obtained in part (a) (0.25 g, 0.5 mmol), pyridine hydrochloride (0.25 g, 2.16 mmol) and a catalytic amount of quinoline was heated at 180° C. for a period of 2.5 h. The reaction mixture was diluted with methanol (25 mL) and basified with solid Na$_2$CO$_3$ to pH 10. The reaction mixture was filtered, and washed with methanol. The organic layer was concentrated and the residue purified by column chromatography using 0.1% ammonia and 4.5% methanol in chloroform as eluent to yield the compound, (+)-trans-2-(2-chloro-4-trifluoromethylphenyl)-5,7-dihydroxy-8-(2-hydroxy-methyl-1-methylpyrrolidin-3-yl)-chromen-4-one, as a yellow solid.

Yield: 0.15 g (63.7%); $^1$H NMR (CDCl$_3$, 300 MHZ): δ 7.99 (m, 2H), 7.83 (d, 1H), 6.65 (s, 1H), 6.41 (s, 1H), 4.24 (m, 1H), 3.90 (m, 2H), 3.70 (m, 1H), 3.60 (m, 1H), 3.41 (m, 1H), 2.99 (s, 3H), 2.54 (m, 1H), 2.28 (m, 1H); MS (ES+): m/z 470 (M+1).

(c) Preparation of (+)-trans-2-(2-chloro-4-trifluoromethylphenyl)-5,7-dihydroxy-8-(2-hydroxymethyl-1-methylpyrrolidin-3-yl)-chromen-4-one Hydrochloride (Compound A or Voruciclib)

The compound as obtained in (b) (0.1 g, 0.2 mmol) was suspended in methanol (2 mL) and treated with ethereal HCl and the organic solvent evaporated to yield the compound, (+)-trans-2-(2-chloro-4-trifluoromethyl-phenyl)-5,7-dihydroxy-8-(2-hydroxy methyl-1-methyl-pyrrolidin-3-yl)-chromen-4-one hydrochloride.

Yield: 0.1 g (92.8%); $^1$H NMR (CDCl$_3$, 300 MHz): δ 8.02 (d, 2H), 7.83 (d, 1H), 6.64 (s, 1H), 6.41 (s, 1H), 4.23 (m, 1H), 3.73 (m, 2H), 3.68 (m, 1H), 3.51 (m, 1H), 3.39 (m, 1H), 2.99 (s, 3H), 2.54 (m, 1H), 2.31 (m, 1H).

Reference Example 2

(a) Preparation of (+)-trans-2-(2-chlorophenyl)-8-(2-hydroxymethyl-1-methyl pyrrolidin-3-yl)-5,7-dimethoxy-chromen-4-one Sodium hydride (50%, 0.54 g, 11.25 mmol) was added in portions to a solution of (−)-trans-1-[2-hydroxy-3-(2-hydroxymethyl-1-methyl pyrrolidin-3-yl)-4,6-dimethoxyphenyl)-ethanone (0.7 g, 2.2 mmol) in dry DMF (15 mL) at 0° C., under nitrogen atmosphere and with stirring. After 10 min., methyl 2-chlorobenzoate (1.15 g., 6.75 mmol) was added. The reaction mixture was stirred at 25° C. for 2 h. Methanol was added carefully below 20° C. The reaction mixture was poured over crushed ice (300 g), acidified with 1:1 HCl (pH 2) and extracted using EtOAc (2×100 mL). The aqueous layer was basified using a saturated Na$_2$CO$_3$ (pH 10) and extracted using CHCl$_3$ (3×200 mL). The organic layer was dried (anhydrous Na$_2$SO$_4$) and concentrated. To the residue, conc. HCl (25 mL) was added and stirred at room temperature for 2 h. The reaction mixture was poured over crushed ice (300 g) and made basic using a saturated aqueous Na$_2$CO$_3$ solution. The mixture was extracted using CHCl$_3$ (3×200 mL). The organic extract was washed with water, dried (anhydrous Na$_2$SO$_4$) and concentrated to obtain the compound, (+)-trans-2-(2-chloro-phenyl)-8-(2-hydroxymethyl-1-methyl-pyrrolidin-3-yl)-5,7-dimethoxy-chromen-4-one.

Yield: 0.67 g (64%); mp: 91-93° C.; $[\alpha]_D^{25}$=+5.8° (c=0.7, methanol); IR (KBr): 3431, 1648, 1598, 1571 cm$^{-1}$; $^1$H NMR (CDCl$_3$, 300 MHZ): δ 7.70 (dd, 1H), 7.52 (m, 1H), 7.45 (m, 2H), 6.50 (s, 1H), 6.44 (s, 1H), 4.17 (m, 1H), 4.00 (s, 3H), 3.97 (s, 3H), 3.64 (dd, 1H), 3.40 (d, 1H), 3.15 (m, 1H), 2.74 (d, 1H), 2.52 (m, 1H), 2.32 (s, 3H), 2.00 (m, 2H); MS (ES+): m/z 430 (M+1).

(b) Preparation of (+)-trans-2-(2-chlorophenyl)-5,7-dihydroxy-8-(2-hydroxy methyl-1-methyl-pyrrolidin-3-yl)-chromen-4-one Molten pyridine hydrochloride (4.1 g, 35.6 mmol) was added to the compound as obtained in part (a) (0.4 g, 0.9 mmol) and heated at 180° C. for 1.5 h. The reaction mixture was cooled to 25° C., diluted with MeOH (10 mL) and basified using Na$_2$CO$_3$ to pH 10. The mixture was filtered and the organic layer was concentrated. The residue was suspended in water (5 mL), stirred for 30 min., filtered and dried to obtain the compound, (+)-trans-2-(2-chloro-phenyl)-5,7-dihydroxy-8-(2-hydroxymethyl-1-methyl-pyrrolidin-3-yl)-chromen-4-one.

Yield: 0.25 g (70%); IR (KBr): 3422, 3135, 1664, 1623, 1559 cm$^{-1}$; $^1$H NMR (CDCl$_3$, 300 MHz): δ 7.56 (d, 1H), 7.36 (m, 3H), 6.36 (s, 1H), 6.20 (s, 1H), 4.02 (m, 1H), 3.70 (m, 2H), 3.15 (m, 2H), 2.88 (m, 1H), 2.58 (s, 3H), 2.35 (m, 1H), 1.88 (m, 1H); MS (ES+): m/z 402 (M+1); Analysis: C$_{21}$H$_{20}$ClNO$_5$ C, 62.24 (62.71); H, 5.07 (4.97); N, 3.60 (3.48); Cl, 9.01 (8.83).

(c) Preparation of (+)-trans-2-(2-chlorophenyl)-5,7-dihydroxy-8-(2-hydroxy methyl-1-methyl-pyrrolidin-3-yl)-chromen-4-one Hydrochloride (Compound B or Riviciclib)

The compound as obtained in part (b) (0.2 g, 0.48 mmol) was suspended in IPA (5 mL) and 3.5% HCl (25 mL) was added. The suspension was heated to get a clear solution. The solution was cooled and solid filtered to obtain the compound, (+)-trans-2-(2-chlorophenyl)-5,7-dihydroxy-8-(2-hydroxymethyl-1-methyl-pyrrolidin-3-yl)-chromen-4-one hydrochloride.

Yield: 0.21 g (97%); mp: 188-192° C.; $[α]_D^{25}$=+21.3° (c=0.2, methanol); $^1$H NMR (CD$_3$OD, 300 MHz): δ 7.80 (d, 1H), 7.60 (m, 3H), 6.53 (s, 1H), 6.37 (s, 1H), 4.23 (m, 1H), 3.89 (m, 2H), 3.63 (m, 1H), 3.59 (dd, 1H), 3.38 (m, 1H), 2.90 (s, 3H), 2.45 (m, 1H), 2.35 (m, 1H); MS (ES+): m/z 402 (M+1) (free base).

Biological Data

Pharmacological Assays:

Example 1

I. In Vitro Study Involving Use of Combination of Compound A (CDK Inhibitor, Also Referred to as Voruciclib) and Vemurafenib (BRAFV600E Inhibitor) in BRAFV600E Mutated Melanoma Cell Lines
Objective:
To study the effect of the combination of compound A (CDK inhibitor, also referred to as voruciclib) and vemurafenib (BRAFV600E inhibitor) on the cell cycle and apoptosis in BRAFV600E mutated melanoma cell lines.
Materials and Methods:
Cell Lines
G361 and SK-MEL3 melanoma cell lines obtained from ATCC (American Type Culture Collection), USA, were used in this study. G361 is vemurafenib sensitive cell line while SK-MEL3 is vemurafenib resistant cell line. Both the cell lines are BRAFV600E mutated.
A. Analysis of Cell Cycle Distribution Using Flow Cytometry:
The G361/SK-MEL3 melanoma cells were seeded in 25 mm$^3$ tissue culture flasks. After 24 h, G361 cells were treated with: i) compound A (1 µM); ii) vemurafenib (1 µM); and iii) compound A (1 µM) and vemurafenib (1 µM) together for 5 days.
In case of SK-MEL3 melanoma cells, the cells were treated with: i) compound A (1 µM); ii) vemurafenib (10 µM); and iii) compound A (1 µM) and vemurafenib (10 µM) together for 5 days.

The control cells were left untreated for 5 days. Both detached and adherent cells were harvested at the end of 5 days. The cells were washed twice with approximately 5 mL of phosphate buffered saline (PBS) with centrifugation at 1000 rpm for 10 min. The cells were resuspended in 500 µL of PBS and fixed in 500 µL ice-cold 70% ethanol. The fixed cells were incubated at room temperature for 30 min, spun at 1000 rpm for 10 min. To the cell pellet, 1 mL of chilled 70% ethanol was added and stored below 0° C. till further analysis. The cells were washed twice with PBS to remove fixative and re-suspended in 250 µL PBS. To this 12.5 µL of propidium iodide (1 mg/ml in PBS) and 12.5 µL Rnase A (1 mg/mL) was added. After incubation at 37° C. for 30 min, the cells were analyzed using flow cytometry.

A flow cytometer (Becton Dickinson FACS Calibur, USA) was used for these studies in accordance with the manufacturer's recommendations. The argon ion laser set at 488 nm was used as an excitation source. Cells with DNA content between 2n and 4n were designated as being in G1, S and G2/M phases of the cell cycle, as defined by the level of red fluorescence. Cells exhibiting less than 2n DNA content were designated as sub-G1 cells. The number of cells in each cell cycle compartment was expressed as a percentage of the total number of cells present.
B. Annexin V-FITC Staining (For the Detection of Early Apoptosis)

Annexin V-FITC is a sensitive probe for identifying apoptotic cells. During early apoptosis, the membrane phospholipid phosphatidyl serine (PS) is translocated from the inner to the outer leaflet of the plasma membrane, thereby exposing PS to the external cellular environment. Annexin V is a 35-36 kDa Calcium dependent phospholipid binding protein that has a high affinity for PS and binds to cells with exposed PS.

Propidium iodide is a polar dye, which enters cells through leaky membranes and hence, is used in conjunction with fluorescein isothiocyanate (FITC) for detection of late apoptosis.

Figure 2:
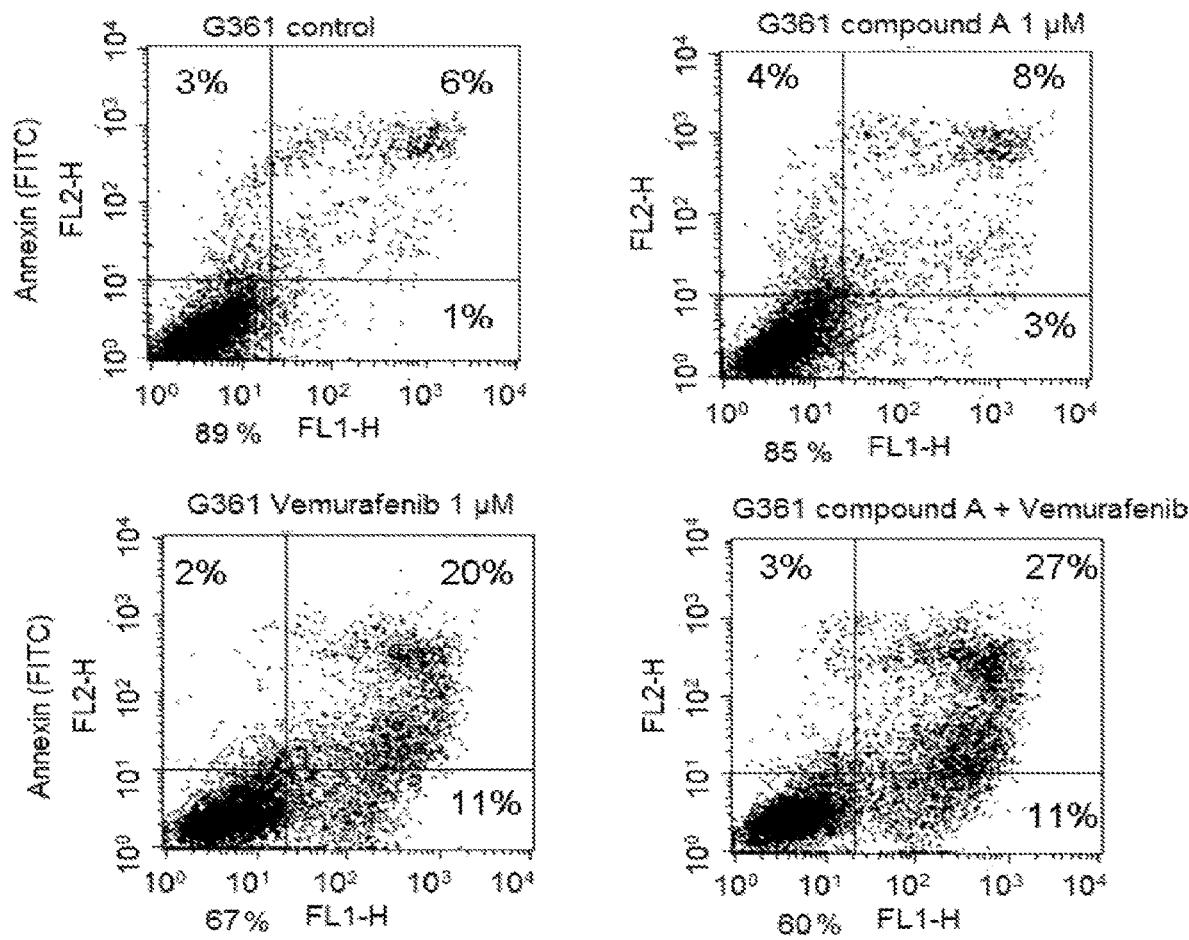
FIG. 2 depicts the effect of compound A (voruciclib) and vemurafenib alone and in combination, on the early apoptosis in G361 melanoma cells treated for 24 h using Annexin staining method.
Figure 3:
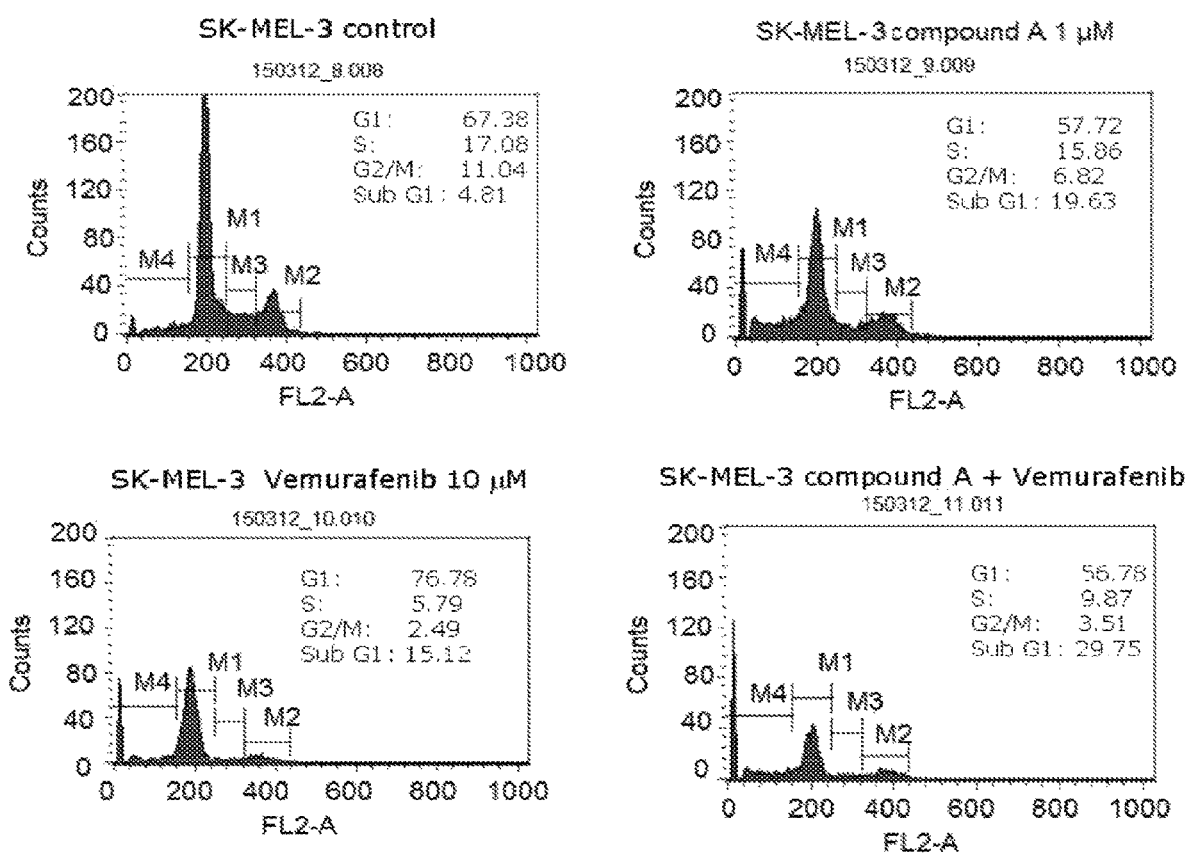
FIG. 3 depicts the effect of compound A (voruciclib) and vemurafenib alone and in combination, on the cell cycle and apoptosis in SK-MEL3 melanoma cells after 5 days using flow cytometry.

The melanoma cells G361 was seeded in 25 mm$^3$ tissue culture flasks. After 24 h, cells were treated with: i) compound A (1 µM); ii) vemurafenib (1 µM); and iii) compound A (1 µM) and vemurafenib (1 µM) together; for 24 h. The control cells were left untreated for 24 h. Medium containing floating cells were collected and pooled with the adherent cells after harvesting with trypsin at the different time points. The cells were washed twice with cold PBS with centrifugation at 1000 rpm for 10 minutes. The cell pellet was resuspended in 1× binding buffer (10 mm HEPES pH 7.4, 140 mM NaCl, 2.5 mM CaCl$_2$) at a concentration of 1×10$^6$ cells/mL. 100 µL of the solution (1×10$^5$ cells) were stained with Annexin V-FITC and propidium iodide. The cells were incubated for 15 min at room temperature (25-30° C.) in the dark and the sample was analysed by flow cytometry.
Results:
The results of these studies are depicted in FIGS. 1-3.
Conclusion:
FIG. 1 indicates that the vemurafenib treated G361 cells show significant G1 arrest of 91.94% vs. control cells (72.36%). As seen from the sub G1 phase the cells treated with compound A and vemurafenib alone showed only 9.48% and 2.3% apoptosis respectively, whereas the cells when treated with the combination of compound A and vemurafenib showed 53.67% cells undergoing apoptosis, indicating that the combination is synergistic.

In FIG. 2, the top right quadrant indicates G361 cells which are in early apoptosis. Subsequently these cells undergo apoptosis leading to cell death. The cells treated with the combination of compound A and vemurafenib showed 27% of cells in early apoptosis (annexin stained cells) versus 8% and 20% for cells treated with only compound A and vemurafenib respectively. This data indicates that the combination exhibits synergy.

In FIG. 3, the SK-MEL3 cells treated with only vemurafenib showed significant G1 arrest of 76.78% versus control cells (67.38%). Apoptosis is seen in 29.75% of the cells treated with the combination of compound A and vemurafenib, as seen from the sub G1 phase while the cells treated with compound A and vemurafenib alone showed only 19.63% and 15.12% apoptosis respectively, indicating that the combination is synergistic.

The results as depicted in FIGS. 1-3 and as explained above, clearly establish that the combination of compound A and vemurafenib is synergistic in the vemurafenib sensitive and resistant BRAFV600E mutated melanoma cell lines and induces greater apoptosis when used in combination as compared to the compound A and vemurafenib when used alone.

II. In Vitro Dual Combination Studies of Compound A with Vemurafenib (BRAFV600E Inhibitor) in Human BRAF-Mutated Melanoma Cells Objective: The objective of this study was to evaluate the efficacy of the combination of compound A (CDK inhibitor) and vemurafenib (BRAFV600E inhibitor) in BRAF mutated melanoma cells.

A. Materials

Test compounds: compound A (prepared in PEL's Lab); vemurafenib (Nanjing Chemlin Chemical Industry Co., Ltd, China)

Vehicle: DMSO (Sigma-Aldrich-Chemie Gmbh, Germany)

Dose Preparation: compound A and vemurafenib were weighed and dissolved in the required amount of DMSO to give a required stock solution.

Test System: Test system included the G361, A375 and MDAMB-435S (BRAFV600E mutated) cell lines, which were procured from ATCC (American Type Culture Collection), USA.

B. Methods

The cytotoxicity studies using compound A and vemurafenib in various combinations, were carried out using the CCK8 live cell dehydrogenase assay.

i) Cell Counting Kit-8 (CCK8) Live Cell Dehydrogenase Assay

The human BRAFV600E mutated melanoma cancer cell lines, G361, A375 and MDAMB-435S were seeded at a density of 3000 cells/well in 199 µL of RPMI 1640 medium in 96-well plate and incubated overnight to allow the cells to adhere. The cells were then treated with the respective test compounds. Totally there were ten groups;

i) 1 µM of vemurafenib alone for 48 h;
ii) 0.3 µM/0.1 µM of compound A alone for 48 h;
iii) 1 µM/0.3 µM of compound A alone for 48 h;
iv) 3 µM/1 µM of compound A alone for 48 h;
v) 10 µM/3 µM of compound A alone for 48 h;
vi) combination of 0.3 µM/0.1 µM of compound A and 1 µM of vemurafenib for 48 h;
vii) combination of 1 µM/0.3 µM of compound A and 1 µM of vemurafenib for 48 h;
viii) combination of 3 µM/1 µM of compound A and 1 µM of vemurafenib for 48 h;
ix) combination of 10 µM/3 µM of compound A and 1 µM of vemurafenib for 48 h;
x) control wells were treated with DMSO vehicle for 48 h.

The plates were incubated in humidified 5% $CO_2$ incubator at 37°±1° C. vemurafenib was used at a concentration of 1.0 µM for all 3 different cell lines, while compound A was used at concentrations of 0.3 µM, 1 µM, 3 µM and 10 µM in case of A375 melanoma cells and at concentrations of 0.1 µM, 0.3 µM, 1.0 µM, 3.0 µM in case of G361 and MDA MB435S melanoma cells. At the end of the incubation periods, the plates were assayed using the CCK8 cytotoxicity assay protocol. The synergism was determined by the combination index (CI) calculated using the Compusyn software by Chou and Talalay (4). CI<1 is synergistic, CI=1 is additive and CI>1 is antagonistic.

Statistical Analysis:

Statistical analysis was performed using the Student t test, and a p value of <0.05 was considered significant. Data are expressed as the mean±standard error of the mean (SEM). The mean value was obtained from at least two independent experiments, each performed in triplicate.

ii) Cytotoxicity Assay Protocol

Logarithmically growing cells were plated at a density of $3×10^3$ cells/well and allowed to recover for 16-18 h. The cells were challenged with varying concentration of both the compounds, compound A and vemurafenib for 48 h. After 48 h, cell toxicity was determined by CCK-8 reagent (Dojindo Molecular Technologies, Inc, Maryland, and Japan). In accordance with the manufacturer's instructions, 5 µL/well CCK-8 reagent was added and plates were incubated for 2 h. The toxicity was determined by measuring the absorbance on Tecan Sapphire multi-fluorescence micro-plate reader at a wavelength of 450 nm corrected to 650 nm and normalized to controls. All the experiments were performed twice in triplicates.

Treatment Schedule for Compound A and Vemurafenib:

Tables 1 and 2 indicate the treatment schedule of compound A and vemurafenib in A375 cells and in G361 and MDA-MB435S cells, respectively.

TABLE 1

Treatment schedule of compound A and vemurafenib in A375 cells

| S. No. | Treatment groups for A375 cells | Treatment schedule (in hours(h)) |
|---|---|---|
| i | compound A (1 µM) | 48 h |
| ii | compound A (0.3 µM) | 48 h |
| iii | compound A (1.0 µM) | 48 h |
| iv | compound A (3.0 µM) | 48 h |
| v | compound A (10.0 µM) | 48 h |
| vi | compound A (0.3 µM) & vemurafenib (1 µM) | 48 h |
| vii | compound A (1.0 µM) & vemurafenib (1 µM) | 48 h |
| viii | compound A (3.0 µM) & vemurafenib (1 µM) | 48 h |
| ix | compound A (10.0 µM) & vemurafenib (1 µM) | 48 h |
| x | Control + Vehicle (DMSO) | 48 h |

TABLE 2

Treatment schedule of compound A and vemurafenib in G361 and MDA-MB435S cells

| S. No. | Treatment groups for G361 & MDA-MB435S cells | Treatment schedule (in hours(h)) |
|---|---|---|
| i | vemurafenib (1 µM) | 48 h |
| ii | compound A (0.1 µM) | 48 h |
| iii | compound A (0.3 µM) | 48 h |
| iv | compound A (1.0 µM) | 48 h |
| v | compound A (3.0 µM) | 48 h |

TABLE 2-continued

Treatment schedule of compound A and vemurafenib in G361 and MDA-MB435S cells

| S. No. | Treatment groups for G361 & MDA-MB435S cells | Treatment schedule (in hours(h)) |
|---|---|---|
| vi | compound A (0.1 µM) & vemurafenib (1 µM) | 48 h |
| vii | compound A (0.3 µM) & vemurafenib (1 µM) | 48 h |
| viii | compound A (1.0 µM) & vemurafenib (1 µM) | 48 h |
| ix | compound A (3.0 µM) & vemurafenib (1 µM) | 48 h |
| x | Control + Vehicle (DMSO) | 48 h |

Figure 4:
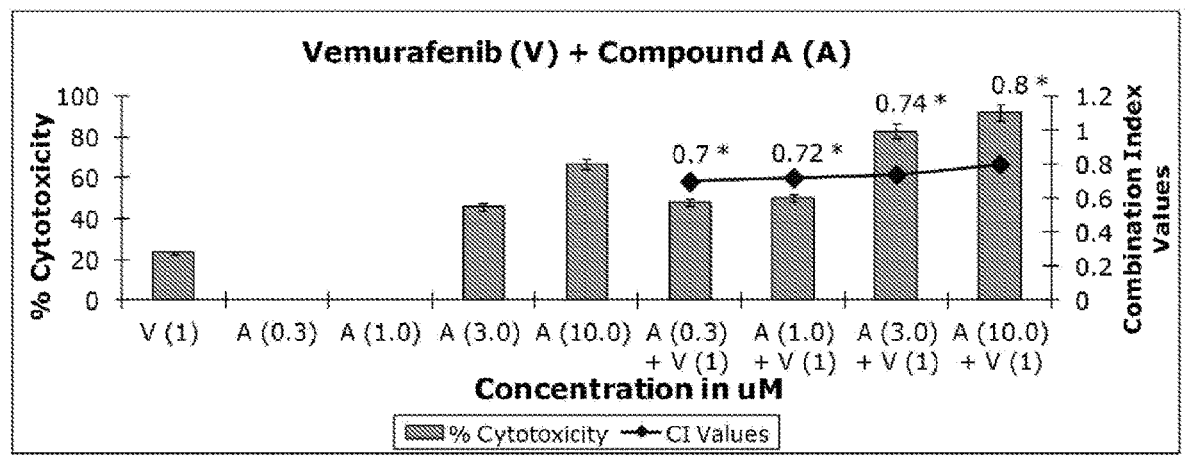
FIG. 4 depicts the effect of compound A (voruciclib) and vemurafenib alone and in combination (48 h), in A375 cell line.
Figure 5:
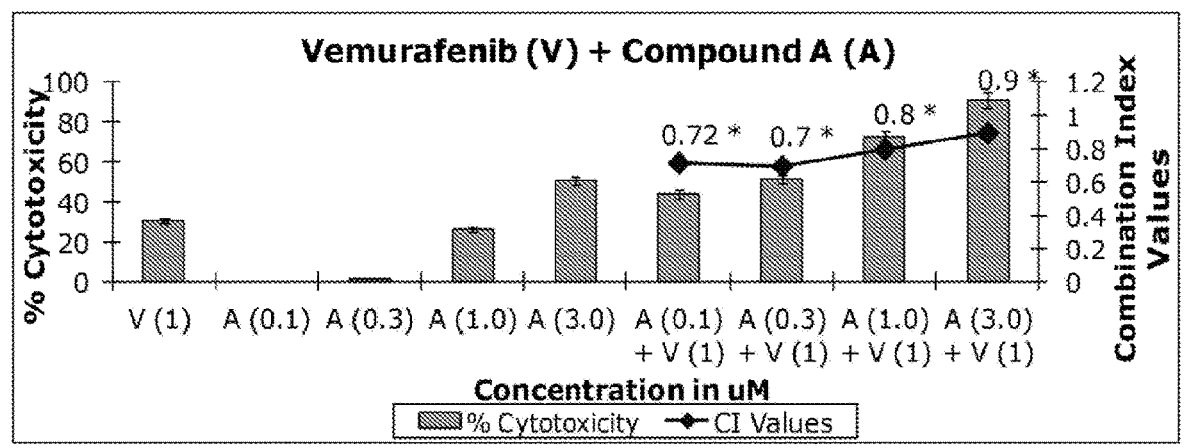
FIG. 5 depicts the effect of compound A (voruciclib) and vemurafenib alone and in combination (48 h), in G361 cell line.
Figure 6:
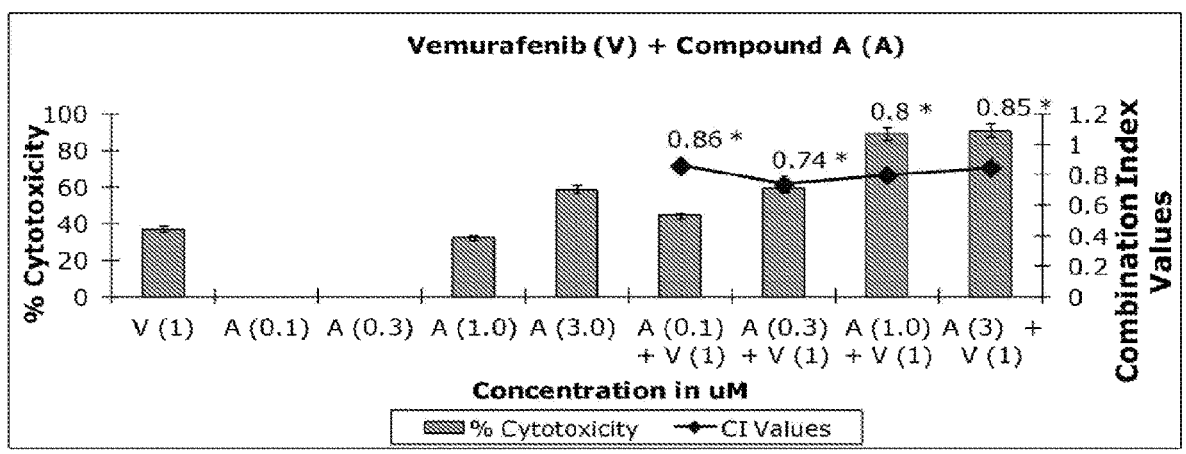
FIG. 6 depicts the effect of compound A (voruciclib) and vemurafenib alone and in combination (48 h), in MDA-MB435S cell line.
Figure 7A:
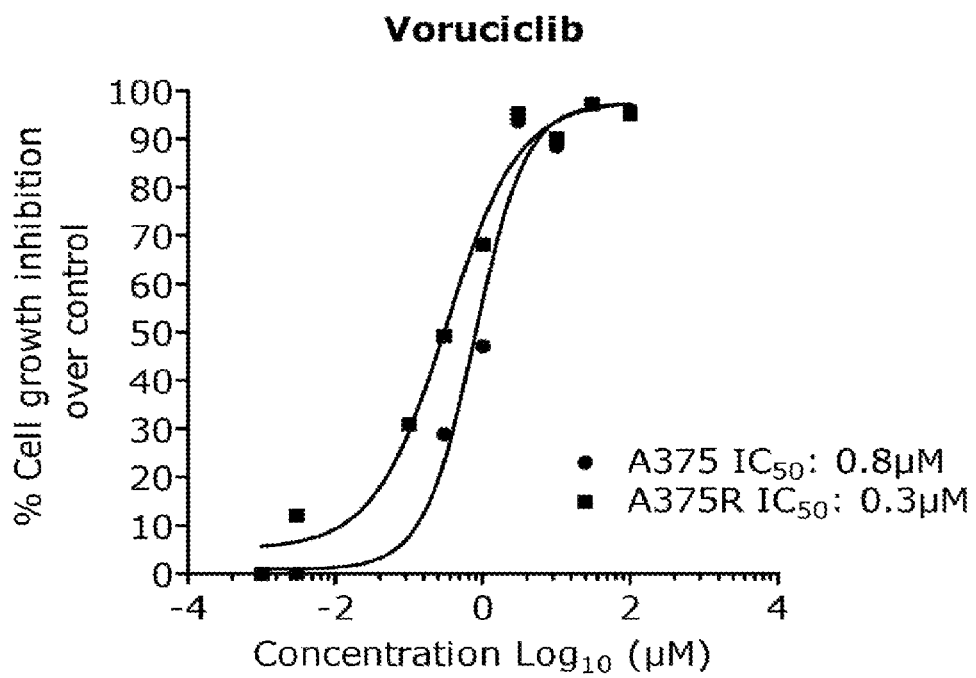
FIGS. 7a and 7b depict the dose response curve of compound A (voruciclib) and vemurafenib alone (48 h) on A375 parental and A375R resistant cell line.
Figure 7B:
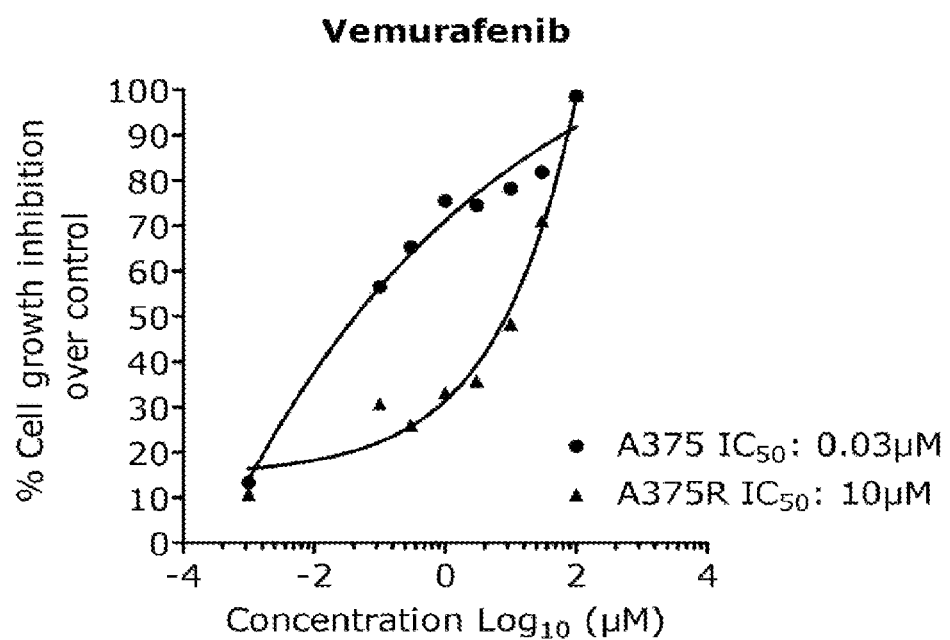
Figure 8A:
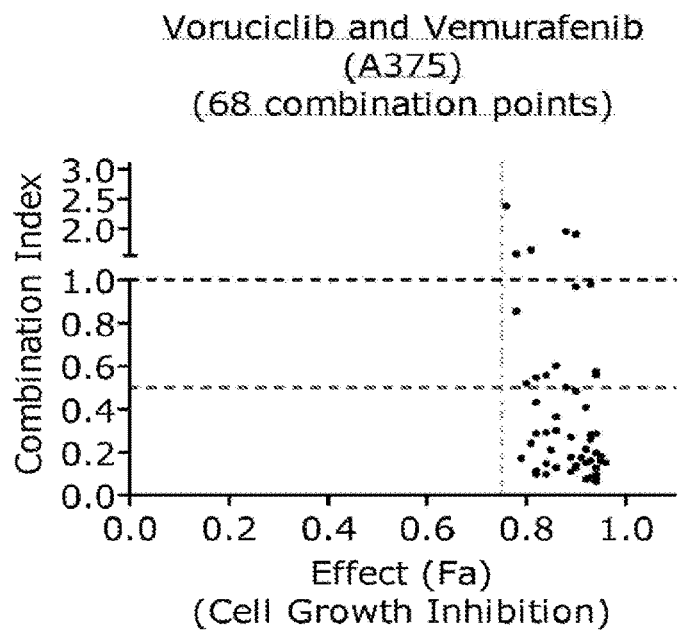
FIGS. 8a and 8b depict the effect of compound A (voruciclib) and vemurafenib alone and in combination (48 h), in A375 resistant cell line.
Figure 8B:
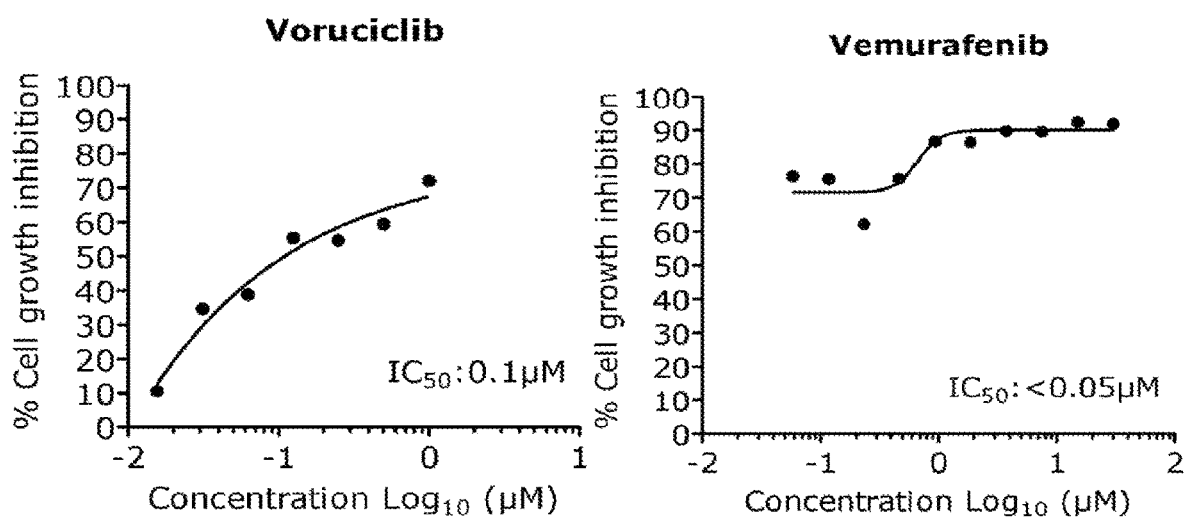
Figure 9A:
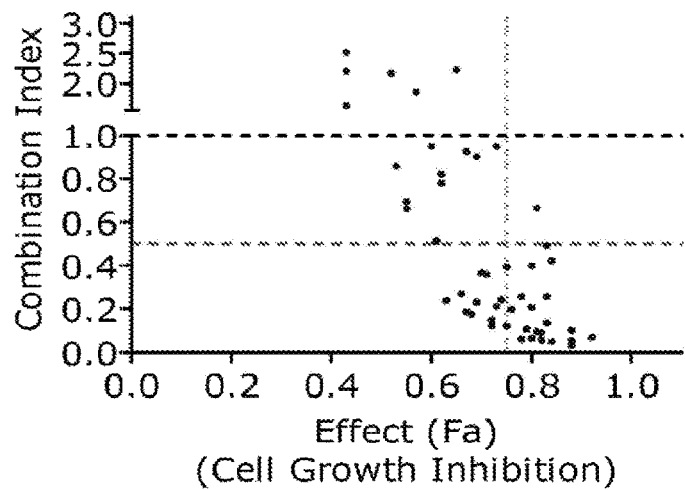
FIGS. 9a and 9b depict the effect of compound A (voruciclib) and vemurafenib alone and in combination (48 h), in A375R resistant cell line.
Figure 9B:
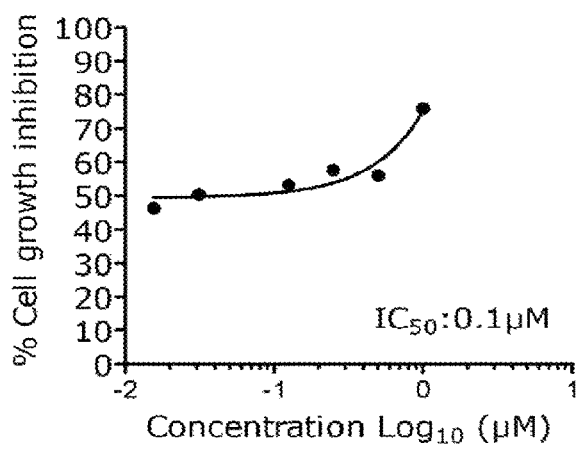
Figure 9B:
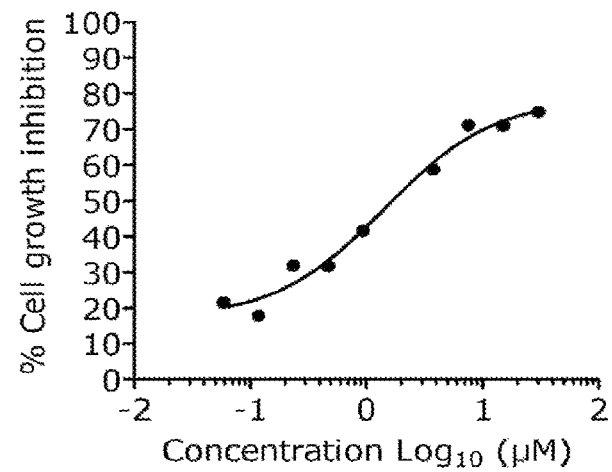
Figure 10A:
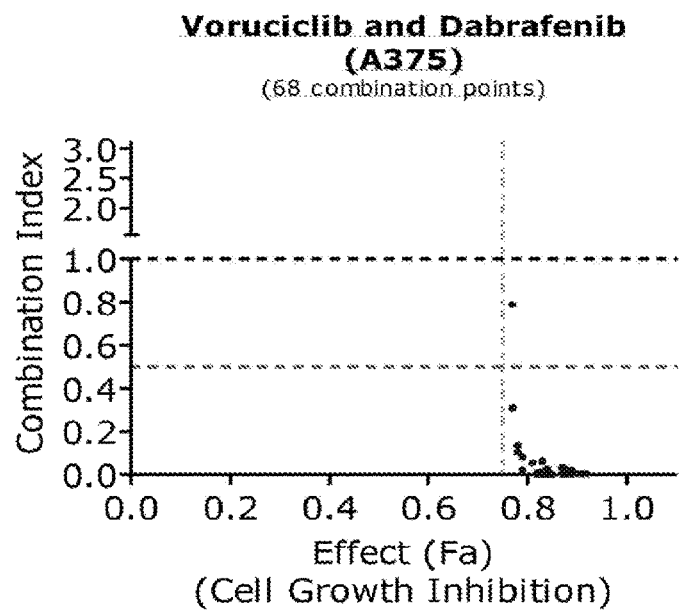
FIGS. 10a and 10b depict the effect of compound A (voruciclib) and trametinib alone and in combination (48 h), in A375 resistant cell line.
Figure 10B:
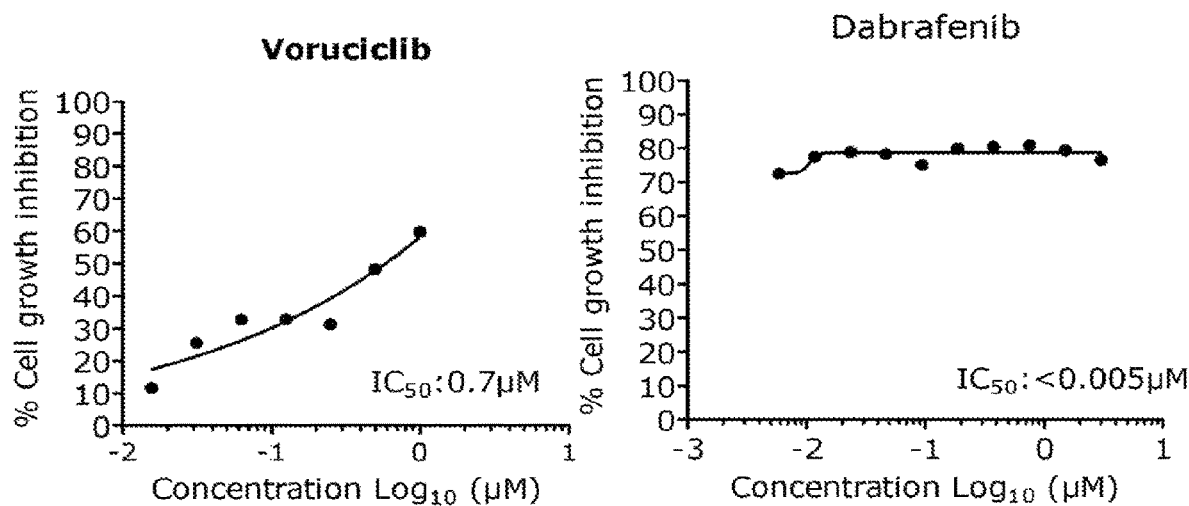
Figure 11A:
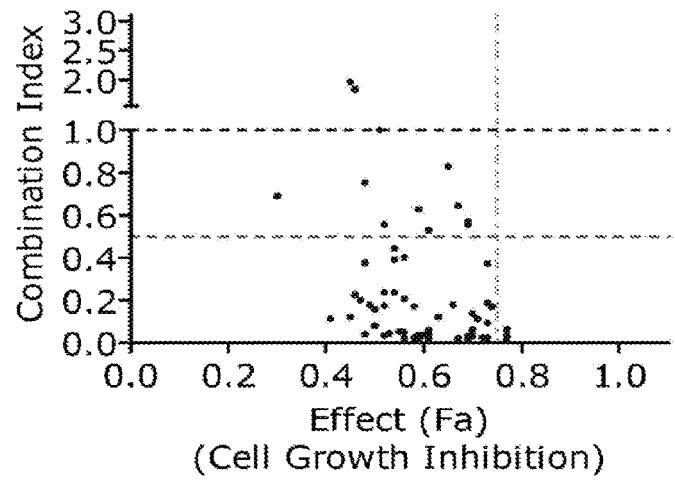
FIGS. 11a and 11b depict the effect of compound A (voruciclib) and trametinib alone and in combination (48 h), in A375R resistant cell line.
Figure 11B:
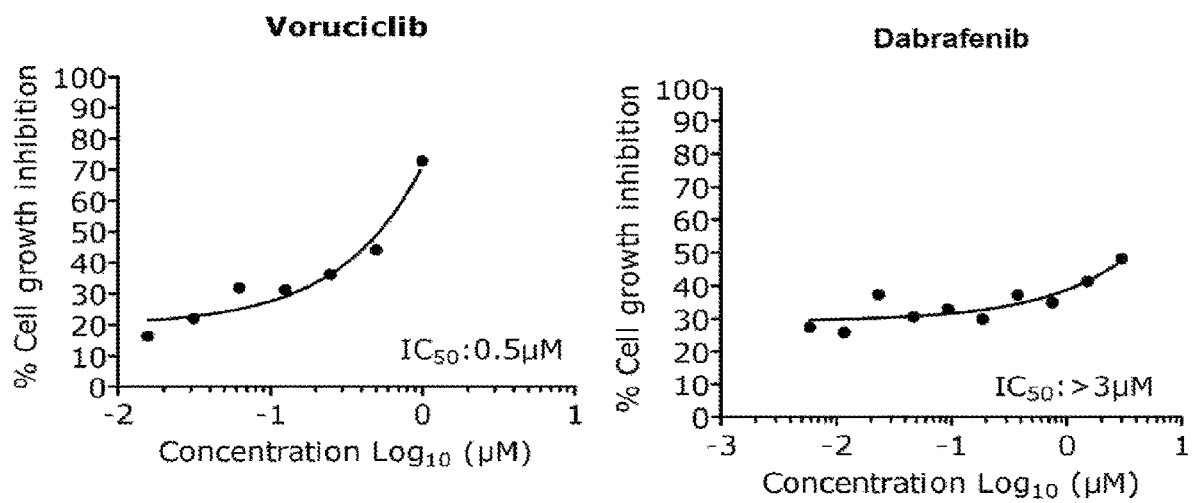
Figure 12A:
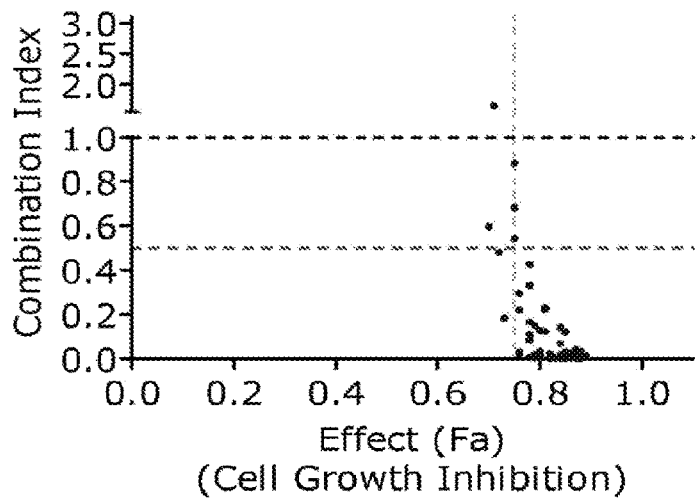
FIGS. 12a and 12b depict the effect of compound A (voruciclib) and dabrafenib alone and in combination (48 h), in A375 resistant cell line.
Figure 12B:
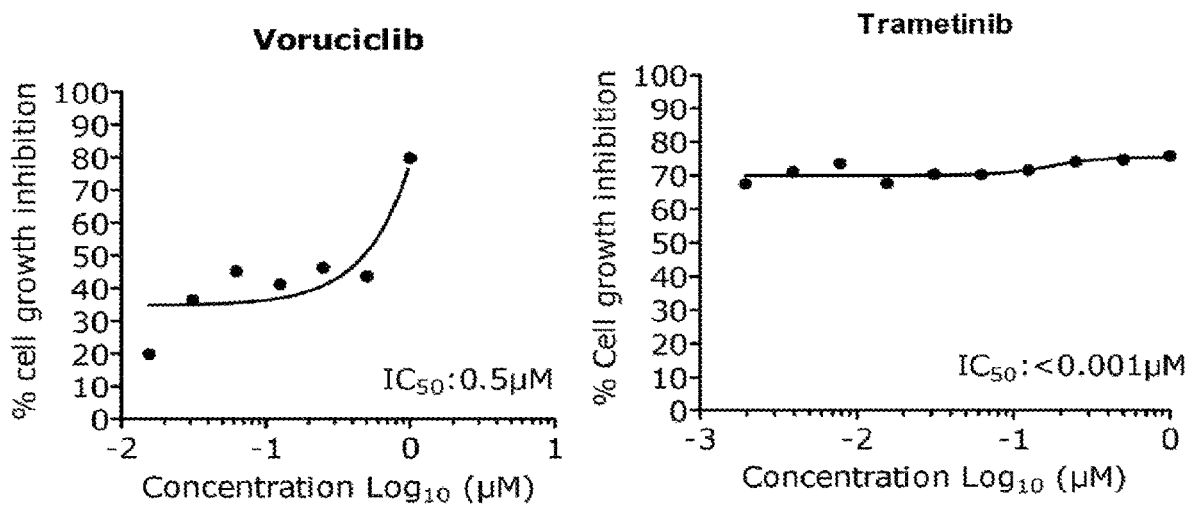
Figure 13A:
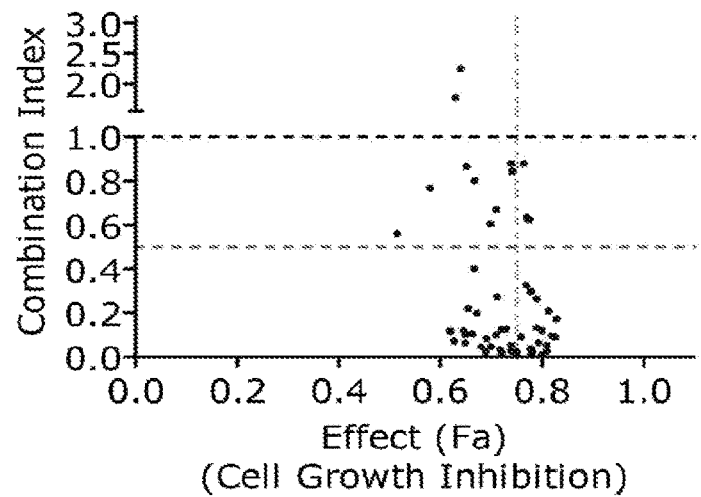
FIGS. 13a and 13b depict the effect of compound A (voruciclib) and dabrafenib alone and in combination (48 h), in A375R resistant cell line.
Figure 13B:
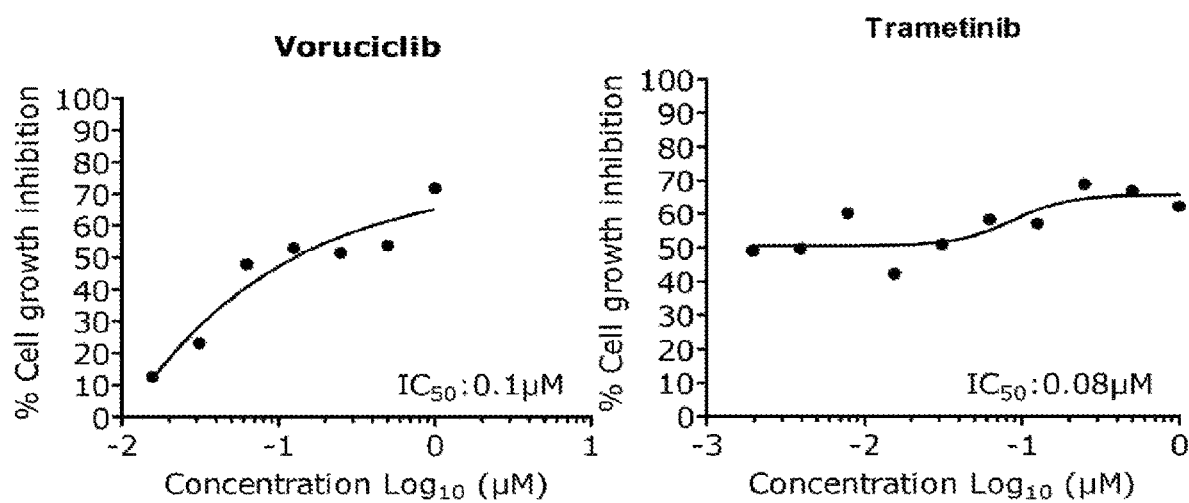

Results:

The $IC_{50}$ values of cytotoxicity for compound A and vemurafenib and combinations thereof in different cell-lines are presented in Table 3. FIGS. 4-6 and Tables 4-6 depict the effect of the combination of compound A and vemurafenib in various melanoma cell-lines.

TABLE 3

$IC_{50}$ determination of compound A and vemurafenib in G361, A375 and MDAMB-435S ($BRAF^{V600E}$ mutated) cell lines

| Sr. No. | Cell line | Compounds | $IC_{50}$ in µM (±SEM) |
|---|---|---|---|
| 1 | A375 | compound A | 5.5 ± 0.67 |
|   |      | compound A | 0.8 ± 0.07 |
| 2 | G361 | compound A | 0.75 ± 0.056 |
|   |      | compound A | 0.2 ± 0.032 |
| 3 | MDAMB435S | compound A | 0.85 ± 0.064 |
|   |           | compound A | 0.7 ± 0.058 |

In FIGS. 4-6, X-axis shows the concentration of compound A and vemurafenib alone and of the compounds in combination, left Y-axis shows % cytotoxicity and right Y-axis shows combination index values.

In FIG. 4, the cells treated with vemurafenib at 1 µM showed 23% inhibition while the cells treated with compound A at 3 µM showed 46% inhibition of cells. However, when the cells were treated with vemurafenib in combination with compound A at this suboptimal concentration, a synergistic effect of 83% inhibition of cells with a combination index (CI) of 0.70 was observed. The exhibited synergistic data represents the mean for two independent experiments, each performed in triplicate.

TABLE 4

Mean combination index values for combination of compound A and vemurafenib in A375 cells

| Concentration in µM | Combination index (95% CI) in A375 cells |
|---|---|
| compound A (0.3 µM) & vemurafenib (1 µM) | 0.66 (0.58 to 0.75) |
| compound A (1.0 µM) & vemurafenib (1 µM) | 0.68 (0.60 to 0.77) |
| compound A (3.0 µM) & vemurafenib (1 µM) | 0.70 (0.62 to 0.79) |
| compound A (10.0 µM) & vemurafenib (1 µM) | 0.76 (0.68 to 0.85) |

CI = Confidence Intervals

In FIG. 5, the cells treated with vemurafenib at 1 µM showed 30% inhibition while the cells treated with compound A at 0.3 µM showed only 2% inhibition of cells. However, when the cells were treated with vemurafenib in combination with compound A at this suboptimal concentration, notable synergistic effect of 52% inhibition of cells with a combination index value of 0.77 was observed. When the cells were treated with compound A (3 µM) in combination with vemurafenib (1 µM), it showed 91% inhibition of cells with a combination index of 0.9. The exhibited synergistic data represents the mean for two independent experiments, each performed in triplicate.

TABLE 5

Mean combination index values for combination of compound A and vemurafenib in G361 cells

| Concentration in µM | Combination index (95% CI) in G361 cells |
|---|---|
| compound A (0.1 µM) & vemurafenib (1 µM) | 0.79 (0.74 to 0.84) |
| compound A (0.3 µM) & vemurafenib (1 µM) | 0.77 (0.72 to 0.82) |
| compound A (1.0 µM) & vemurafenib (1 µM) | 0.87 (0.82 to 0.92) |
| compound A (3.0 µM) & vemurafenib (1 µM) | 0.97 (0.92 to 1.02) |

CI = Confidence intervals

In FIG. 6, the cells treated with vemurafenib at 1 µM showed 31% inhibition of cells while the cells treated with compound A at 1 µM showed 32% inhibition of cells. When the cells were treated with vemurafenib in combination with compound A at this suboptimal concentration, synergistic effect of 90% inhibition of cells with a combination index of 0.74 was noted. The exhibited synergistic data represents the mean for two independent experiments, each performed in triplicate.

TABLE 6

Mean combination index values for combination of compound A and vemurafenib in MDA MB-435S cells

| Concentration in µM | Combination index (95% CI) in MDA-MB435S cells |
|---|---|
| compound A (0.1 µM) & vemurafenib (1 µM) | 0.83 (0.78 to 0.88) |
| compound A (0.3 µM) & vemurafenib (1 µM) | 0.78 (0.72 to 0.83) |
| compound A (1.0 µM) & vemurafenib (1 µM) | 0.74 (0.68 to 0.79) |
| compound A (3.0 µM) & vemurafenib (1 µM) | 0.90 (0.85 to 0.96) |

CI = Confidence Intervals

Conclusion:

The combination of vemurafenib and compound A showed a marked synergistic effect in BRAF mutated melanoma cells.

REFERENCES

1. Smalley K S, Lioni M, Palma M D, Xiao M, Desai B, Egyhazi S, Hansson J, Wu H, King A J, Van Belle P, Elder D E, Flaherty K T, Herlyn M, Nathanson K L; "Increased cyclin D1 expression can mediate BRAF inhibitor resistance in BRAF V600E-mutated melanomas"; Mol. Cancer Ther., 2008, 7, 2876-2883.
2. Smalley K S M and Flaherty K T; "Integrating BRAF/MEK inhibitors into combination therapy for Melanoma'; British Journal of Cancer, 2009, 100, 431-435.
3. Dhomen N, Marais R; "BRAF signaling and targeted therapies in melanoma" Hematol. Oncol. Clin. North Am., 2009, 23, 3, 529-45.
4. Ting-Chao Chou; "Theoretical basis, experimental design, and computerized simulation of synergism and antagonism in drug combination studies" Pharmacol. Rev., 2006, 58, 621-81.

Example 2

A. In Vitro Combination Studies of Compound A (CDK Inhibitor, Also Referred to as Voruciclib) With One Anticancer Agent Selected From a BRAF Inhibitor (Vemurafenib or Dabrafenib) or a MEK Inhibitor (Trametinib) in a Human BRAF-V600E Mutated Melanoma Cell Line (A375) and its Vemurafenib Resistant Derivative (A375R)

Objective:

The objective of this study was to evaluate the efficacy of the combination of CDK inhibitor (voruciclib) with a BRAF inhibitor (vemurafenib or dabrafenib) or a MEK inhibitor (trametinib) in BRAF mutated melanoma cells.

B. Materials:

Test Compounds: compound A (prepared in PEL's Lab.); vemurafenib (Selleckchem USA, S1267); dabrafenib (Selleckchem USA, S2807) and trametinib (Selleckchem USA, S2673)

Vehicle: DMSO (Sigma-Aldrich-Chemie Gmbh, Germany)

Dose Preparation: The test compounds were weighed and dissolved in the required amount of DMSO to give a required stock solution.

Test System: Test system included the A375 (BRAFV600E mutated) cell line, which were procured from ATCC (American Type Culture Collection), USA and A375R cell line (vemurafenib resistant—developed in PEL's Lab.)

C. Methods:

The cytotoxicity studies using all the test compounds as single agents and in combinations were carried out using the CCK8 live cell dehydrogenase assay.

Cell Counting Kit-8 (CCK8) Live Cell Dehydrogenase Assay:

Logarithmically growing human BRAFV600E mutated melanoma cells were seeded at a density of 1500 cells/well in 30 μL of Dulbecco's Modified Eagle medium medium (DMEM) in 384-well plate (Corning, USA) using Tecan automated platform (FreedomEvo Liquid handling system) and incubated for about 12-16 h to allow the cells to adhere. The cells were then treated for 48 h with different doses of compound A and anticancer agents (vemurafenib or dabrafenib or trametinib) as monotherapy (used singly) and in combinations. Studies using different dosages were carried out for each combination (e.g. combination of compound A and vemurafenib). The treatment ratios of the test compounds when used singly and in combination in A375 and A375R cells are depicted in tables 7A-7C (i.e. combination of compound A and vemurafenib; combination of compound A and dabrafenib; and combination of compound A and trametinib). The following doses of compound A (μM): 1, 0.5, 0.25, 0.125, 0.06, 0.03, 0.015; vemurafenib (μM) 30, 15, 7.5, 3.75, 1.875, 0.9, 0.4, 0.2, 0.1, 0.05; dabrafenib (μM) 3, 1.5, 0.75, 0.37, 0.18, 0.09, 0.04, 0.02, 0.01, 0.005; trametinib (μM) 1, 0.5, 0.25, 0.125, 0.0625, 0.031, 0.015, 0.007, 0.003, 0.001, were used. The above doses of anticancer agents (vemurafenib or dabrafenib or trametinib) were mixed in multiple ratios with compound A as shown in tables 7A-7C. The controls used were only cells or cells along with the vehicle (DMSO).

The plates were incubated for 48 h in humidified 5% $CO_2$ incubator at 37°±1° C. Post incubation the plates were assayed using the CCK8 reagent (Dojindo Molecular Technologies, Inc, Maryland, and Japan). In accordance with the manufacturer's instructions, 3 μL CCK-8 reagent was added in each well of the 384 well plate and plates were incubated for 2 h. The toxicity was determined by measuring the absorbance on Tecan Sapphire multi-fluorescence microplate reader at a wavelength of 450 nm normalized to controls. All the experiments were performed in quadruplets.

The potency of the combination was quantified using Calcusyn software (Biosoft, Ferguson, MO, USA) which is based on the Chou Talalay method that calculates a combination index (CI) with CI values less than 1 indicating synergy.

Table 7A-7C: Treatment ratios of compound A and anticancer agents (vemurafenib or dabrafenib or trametinib) as monotherapy (used singly) and in combinations in A375 and A375R cells.

The treatment ratios of compound A (denoted as A) and vemurafenib (denoted as V) alone or in combinations are represented in table 7A.

TABLE 7A

| Concentrations in μM | | | | | |
|---|---|---|---|---|---|
| A (0) | V (30) | V (15) | V (7.5) | V (3.75) | V (1.88) |
| A (1) | A (1) + V (30) | A (1) + V (15) | A (1) + V (7.5) | A (1) + V (3.75) | A (1) + V (1.88) |
| A (0.5) | A (0.5) + V (30) | A (0.5) + V (15) | A (0.5) + V (7.5) | A (0.5) + V (3.75) | A (0.5) + V (1.88) |
| A (0.25) | A (0.25) + V (30) | A (0.25) + V (15) | A (0.25) + V (7.5) | A (0.25) + V (3.75) | A (0.25) + V (1.88) |
| A (0.125) | A (0.125) + V (30) | A (0.125) + V (15) | A (0.125) + V (7.5) | A (0.125) + V (3.75) | A (0.125) + V (1.88) |
| A (0.0625) | A (0.0625) + V (30) | A (0.0625) + V (15) | A (0.0625) + V (7.5) | A (0.0625) + V (3.75) | A (0.0625) + V (1.88) |
| A (0.0312) | A (0.0312) + V (30) | A (0.0312) + V (15) | A (0.0312) + V (7.5) | A (0.0312) + V (3.75) | A (0.0312) + V (1.88) |
| A (0.0156) | A (0.0156) + V (30) | A (0.0156) + V (15) | A (0.0156) + V (7.5) | A (0.0156) + V (3.75) | A (0.0156) + V (1.88) |
| A (0) | V (0.94) | V (0.47) | V (0.23) | V (0.12) | V (0.059) |
| A (1) | A (1) + V (0.94) | A (1) + V (0.47) | A (1) + V (0.23) | A (1) + V (0.12) | A (1) + V (0.059) |
| A (0.5) | A (0.5) + V (0.94) | A (0.5) + V (0.47) | A (0.5) + V (0.23) | A (0.5) + V (0.12) | A (0.5) + V (0.059) |
| A (0.25) | A (0.25) + V (0.94) | A (0.25) + V (0.47) | A (0.25) + V (0.23) | A (0.25) + V (0.12) | A (0.25) + V (0.059) |
| A (0.125) | A (0.125) + V (0.94) | A (0.125) + V (0.47) | A (0.125) + V (0.23) | A (0.125) + V (0.12) | A (0.125) + V (0.059) |
| A (0.0625) | A (0.0625) + V (0.94) | A (0.0625) + V (0.47) | A (0.0625) + V (0.23) | A (0.0625) + V (0.12) | A (0.0625) + V (0.059) |
| A (0.0312) | A (0.0312) + V (0.94) | A (0.0312) + V (0.47) | A (0.0312) + V (0.23) | A (0.0312) + V (0.12) | A (0.0312) + V (0.059) |
| A (0.0156) | A (0.0156) +V (0.94) | A (0.0156) + V (0.47) | A (0.0156) + V (0.23) | A (0.0156) + V (0.12) | A (0.0156) + V (0.059) |

The treatment ratios of compound A (denoted as A) and dabrafenib (denoted as D) alone or in combinations are represented in table 7B.

TABLE 7B

| \ | \ | \ | Concentrations in μM | \ | \ |
|---|---|---|---|---|---|
| A (0) | D (3) | D (1.5) | D (0.75) | D (0.38) | D (0.19) |
| A (1) | A (1) + D (3) | A (1) + D (1.5) | A (1) + D (0.75) | A (1) + D (0.38) | A (1) + D (0.19) |
| A (0.5) | A (0.5) + D (3) | A (0.5) + D (1.5) | A (0.5) + D (0.75) | A (0.5) + D (0.38) | A (0.5) + D (0.19) |
| A (0.25) | A (0.25) + D (3) | A (0.25) + D (1.5) | A (0.25) + D (0.75) | A (0.25) + D (0.38) | A (0.25) + D (0.19) |
| A (0.125) | A (0.125) + D (3) | A (0.125) + D (1.5) | A (0.125) + D (0.75) | A (0.125) + D (0.38) | A (0.125) + D (0.19) |
| A (0.0625) | A (0.0625) + D (3) | A (0.0625) + D (1.5) | A (0.0625) + D (0.75) | A (0.0625) + D (0.38) | A (0.0625) + D (0.19) |
| A (0.0312) | A (0.0312) + D (3) | A (0.0312) + D (1.5) | A (0.0312) + D (0.75) | A (0.0312) + D (0.38) | A (0.0312) + D (0.19) |
| A (0.0156) | A (0.0156) + D (3) | A (0.0156) + D (1.5) | A (0.0156) + D (0.75) | A (0.0156) + D (0.38) | A (0.0156) + D (0.19) |
| A (0) | D (0.094) | D (0.047) | D (0.023) | D (0.012) | D (0.006) |
| A (1) | A (1) + D (0.094) | A (1) + D (0.047) | A (1) + ) D (0.023 | A (1) + D (0.012) | A (1) + D (0.006) |
| A (0.5) | A (0.5) + D (0.094) | A (0.5) + D (0.047) | A (0.5) + D (0.023) | A (0.5) + D (0.012) | A (0.5) + D (0.006) |
| A (0.25) | A (0.25) + D (0.094) | A (0.25) + D (0.047) | A (0.25) + D (0.023) | A (0.25) + D (0.012) | A (0.25) + D (0.006) |
| A (0.125) | A (0.125) + D (0.094) | A (0.125) + D (0.047) | A (0.125) + D (0.023) | A (0.125) + D (0.012) | A (0.125) + D (0.006) |
| A (0.0625) | A (0.0625) + D (0.094) | A (0.0625) + D (0.047) | A (0.0625) + D (0.023) | A (0.0625) + D (0.012) | A (0.0625) + D (0.006) |
| A (0.0312) | A (0.0312) + D (0.094) | A (0.0312) + D (0.047) | A (0.0312) + D (0.023) | A (0.0312) + D (0.012) | A (0.0312) + D (0.006) |
| A (0.0156) | A (0.0156) + D (0.094) | A (0.0156) + D (0.047) | A (0.0156) + D (0.023) | A (0.0156) + D (0.012) | A (0.0156) + D (0.006) |

The treatment ratios of compound A (denoted as A) and trametinib (denoted as T) alone or in combinations are represented in table 7C.

TABLE 7C

| \ | \ | \ | Concentrations in μM | \ | \ |
|---|---|---|---|---|---|
| A (0) | T (1) | T (0.5) | T (0.25) | T (0.13) | T (0.06) |
| A (1) | A (1) + T (1) | A (1) + T (0.5) | A (1) + T (0.25) | A (1) + T (0.13) | A (1) + T (0.06) |
| A (0.5) | A (0.5) + T (1) | A (0.5) + T (0.5) | A (0.5) + T (0.25) | A (0.5) + T (0.13) | A (0.5) + T (0.06) |
| A (0.25) | A (0.25) + T (1) | A (0.25) + T (0.5) | A (0.25) + T (0.25) | A (0.25) + T (0.13) | A (0.25) + T (0.06) |
| A (0.125) | A (0.125) + T (1) | A (0.125) + T (0.5) | A (0.125) + T (0.25) | A (0.125) + T (0.13) | A (0.125) + T (0.06) |
| A (0.0625) | A (0.0625) + T (1) | A (0.0625) + T (0.5) | A (0.0625) + T (0.25) | A (0.0625) + T (0.13) | A (0.0625) + T (0.06) |
| A (0.0312) | A (0.0312) + T (1) | A (0.0312) + T (0.5) | A (0.0312) + T (0.25) | A (0.0312) + T (0.13) | A (0.0312) + T (0.06) |
| A (0.0156) | A (0.0156) + T (1) | A (0.0156) + T (0.5) | A (0.0156) + T (0.25) | A (0.0156) + T (0.13) | A (0.0156) + T (0.06) |
| A (0) | T (0.031) | T (0.016) | T (0.008) | T (0.004) | T (0.002) |
| A (1) | A (1) + T (0.031) | A (1) + T (0.016) | A (1) + T (0.008) | A (1) + T (0.004) | A (1) + T (0.002) |
| A (0.5) | A (0.5) + T (0.031) | A (0.5) + T (0.016) | A (0.5) + T (0.008) | A (0.5) + T (0.004) | A (0.5) + T (0.002) |
| A (0.25) | A (0.25) + T (0.031) | A (0.25) + T (0.016) | A (0.25) + T (0.008) | A (0.25) + T (0.004) | A (0.25) + T (0.002) |
| A (0.125) | A (0.125) + T (0.031) | A (0.125) + T (0.016) | A (0.125) + T (0.008) | A (0.125) + T (0.004) | A (0.125) + T (0.002) |
| A (0.0625) | A (0.0625) + T (0.031) | A (0.0625) + T (0.016) | A (0.0625) + T (0.008) | A (0.0625) + T (0.004) | A (0.0625) + T (0.002) |
| A (0.0312) | A (0.0312) + T (0.031) | A (0.0312) + T (0.016) | A (0.0312) + T (0.008) | A (0.0312) + T (0.004) | A (0.0312) + T (0.002) |
| A (0.0156) | A (0.0156) + T (0.031) | A (0.0156) + T (0.016) | A (0.0156) + T (0.008) | A (0.0156) + T (0.004) | A (0.0156) + T (0.002) |

Results:
The results of these studies are depicted in FIGS. 7-13.
Conclusion:
1. From FIGS. 7a and 7b, it can be concluded that A375 cell line is very sensitive to vemurafenib whereas A375R is resistant. Further, both A375 and A375R are equally sensitive to compound A (voruciclib).
2. From FIGS. 8a and 8b, it can be concluded that the combination of compound A (voruciclib) and vemurafenib shows a strong synergy (CI<0.5) in A375 cell line.
3. From FIGS. 9a and 9b, it can be concluded that the combination of compound A (voruciclib) and vemurafenib shows a strong synergy (CI<0.5) in A375R cell line.
4. From FIGS. 10a and 10b, it can be concluded that the combination of compound A (voruciclib) and dabrafenib shows a strong synergy (CI<0.5) in A375 cell line.
5. From FIGS. 11a and 11b, it can be concluded that the combination of compound A (voruciclib) and dabrafenib shows a strong synergy (CI<0.5) in A375R cell line.
6. From FIGS. 12a and 12b, it can be concluded that the combination of compound A (voruciclib) and trametinib shows a strong synergy (CI<0.5) in A375 cell line.
7. From FIGS. 13a and 13b, it can be concluded that the combination of compound A (voruciclib) and trametinib shows a strong synergy (CI<0.5) in A375R cell line.

We claim:

1. A pharmaceutical combination for the treatment of melanoma, the combination comprising a therapeutically effective amount of a CDK (cyclin dependent kinase) inhibitor of formula I or a pharmaceutically acceptable salt thereof;

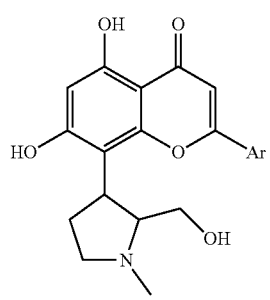

Formula I wherein Ar is 2 chloro-4-trifluoromethylphenyl; and a therapeutically effective amount of at least one anticancer agent selected from vemurafenib, dabrafenib, and trametinib.

2. The pharmaceutical combination according to claim 1, wherein the CDK inhibitor is (+)-trans-2-(2-chloro-4-trifluoromethylphenyl)-5,7-dihydroxy-8-(2-hydroxymethyl-1-methyl-pyrrolidin-3-yl)-chromen-4-one hydrochloride.

3. The pharmaceutical combination according to claim 1, wherein the anticancer agent is vemurafenib.

4. The pharmaceutical combination according to claim 1, wherein the anticancer agent is dabrafenib.

5. The pharmaceutical combination according to claim 1, wherein the anticancer agent is trametinib.

6. The pharmaceutical combination according to claim 1, wherein the CDK inhibitor and the at least one anticancer agent are administered simultaneously to a subject in need thereof.

7. The pharmaceutical combination according to claim 1, wherein the CDK inhibitor and the at least one anticancer agent are administered sequentially to a subject in need thereof.

8. The pharmaceutical combination according to claim 1, wherein the melanoma is non-refractory melanoma.

9. The pharmaceutical combination according to claim 8, wherein the melanoma is non-refractory BRAF mutant melanoma.

10. The pharmaceutical combination according to claim 9, wherein the melanoma is non-refractory BRAFV600 mutant melanoma.

11. The pharmaceutical combination according to claim 10, wherein the melanoma is non-refractory BRAFV600E or BRAFV600K mutant melanoma.

12. The pharmaceutical combination according to claim 1, wherein the melanoma is recurrent or refractory melanoma.

13. The pharmaceutical combination according to claim 12, wherein the melanoma is recurrent or refractory BRAF mutant melanoma.

14. The pharmaceutical combination according to claim 13, wherein the melanoma is recurrent or refractory BRAFV600 mutant melanoma.

15. The pharmaceutical combination according to claim 14, wherein the melanoma is recurrent or refractory BRAFV600E melanoma or BRAFV600K mutant melanoma.

16. The pharmaceutical combination according to claim 1, wherein the melanoma is metastatic melanoma.

17. The pharmaceutical combination according to claim 16, wherein the melanoma is metastatic BRAF mutant melanoma.

18. The pharmaceutical combination according to claim 17, wherein the melanoma is metastatic BRAFV600 mutant melanoma.

19. The pharmaceutical combination according to claim 18, wherein the melanoma is metastatic BRAFV600E melanoma or BRAFV600K mutant melanoma.

* * * * *